(12) United States Patent
Hung et al.

(10) Patent No.: US 10,221,169 B2
(45) Date of Patent: Mar. 5, 2019

(54) SUBSTITUTED AMINOTHIAZOLES FOR THE TREATMENT OF TUBERCULOSIS

(71) Applicants: THE BROAD INSTITUTE, INC., Cambridge, MA (US); The General Hospital Corporation, Boston, MA (US); The Brigham and Women'ts Hospital, Inc., Boston, MA (US)

(72) Inventors: Deborah Hung, Cambridge, MA (US); Michael Serrano-Wu, Belmont, MA (US); Sarah Grant, Boston, MA (US); Tomohiko Kawate, Cambridge, MA (US)

(73) Assignees: The Broad Institute, Inc., Cambridge, MA (US); The General Hospital Corporation, Boston, MA (US); The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 15/467,432

(22) Filed: Mar. 23, 2017

(65) Prior Publication Data
US 2017/0305895 A1    Oct. 26, 2017

Related U.S. Application Data

(62) Division of application No. 14/776,521, filed as application No. PCT/US2014/025488 on Mar. 13, 2014, now abandoned.

(60) Provisional application No. 61/779,101, filed on Mar. 13, 2013.

(51) Int. Cl.
| | |
|---|---|
| *C07D 417/14* | (2006.01) |
| *C07D 417/04* | (2006.01) |
| *C07D 417/12* | (2006.01) |
| *C07D 277/50* | (2006.01) |

(52) U.S. Cl.
CPC ......... *C07D 417/14* (2013.01); *C07D 277/50* (2013.01); *C07D 417/04* (2013.01); *C07D 417/12* (2013.01)

(58) Field of Classification Search
CPC .................................................... C07D 417/14
USPC .......................................................... 514/365
See application file for complete search history.

(56) References Cited

U.S. PATENT DOCUMENTS

| | | |
|---|---|---|
| 8,022,222 B2 | 9/2011 | Aicher |
| 2005/0227989 A1 | 10/2005 | Wang |
| 2009/0053192 A1 | 2/2009 | Millan et al. |
| 2014/0249154 A1 | 9/2014 | Cuconati |

OTHER PUBLICATIONS

Ananthan et al., Tuberculosis (2009), vol. 89, pp. 334-353. Cited in ISR of pct/us14/025488.*
Wayne et al., Annu. Rev. Microbiol. (2001), vol. 55:139-163.*
International Search Report/Written Opinion for corresponding PCT/US2014/25488 dated Aug. 28, 2014.
Ananthan, Subramaniam et al. "High-throughput Screening for Inhbitors of *Mycobacterium tuberculosis* H37Rv", Tuberculosis 89, pp. 334-353 (2009).
Gallardo-Godoy et al., "2-Aminothiazoles, etc." J. Med. Chem., 2011, 54 pp. 1010-1121.
Manuvakhova et al., "Identification of Novel, etc.,"Journal of Neurosecience Research 89: pp. 58-72 (2011).
Gentles et al., "Initial SAR studies, etc.,"Bioorganic & Medicinal Chemistry Letters 18 pp. 5316-5319 (2008).
Goodwin, "Metal chelates, etc.," CA 62:27401 1965.
Ettmayer et al. "Lessons Learned from Marketed and Investigational Prodrugs.", J. Med. Chem., (2004), 47(10) pp. 2393-2404.
Stella, Valentino, "Prodrugs as therapeutics." Expert Opin. Ther. Patents (2004), 14(3) pp. 277-280.
Testa, Bernard, "Prodrug research: futile or Fertile?" Biochemical Pharmacology, 68 (2004), pp. 2097-2106.
Wolff, ed., Burger's Medicinal Chemistry and Frug Discovery, 5th edition, NY: John Wiley & Sons, 996, vol. 1, pp. 949-976.
Jordan "Tamoxifen . . . " Nature Rev. v.2, pp. 205-213 (2003).

* cited by examiner

*Primary Examiner* — Taofiq A Solola
(74) *Attorney, Agent, or Firm* — Thomas J. Engellenner; Reza Mollaaghababa; Pepper Hamilton LLP

(57) ABSTRACT

Disclosed ore substituted aminothiazoles, which can be used for, among other things, the treatment of tuberculosis, pharmaceutical compositions containing the same, and methods of using the same.

13 Claims, No Drawings

SUBSTITUTED AMINOTHIAZOLES FOR THE TREATMENT OF TUBERCULOSIS

CROSS REFERENCE TO RELATED APPLICATIONS

The present application is a division of U.S. application Ser. No. 14/776,521, filed Sep. 14, 2015, which is a U.S. National 371 Application of PCT/US2014/025488, filed Mar. 13, 2014, which claims benefit to U.S. Provisional Patent Application No. 61/779,101, filed Mar. 13, 2013, the contents of which are incorporated herein by reference in their entireties.

The present application claims priority to U.S. Provisional Application No. 61/779,101, filed Mar. 13, 2013, which is hereby incorporated by reference in its entirety.

REFERENCE TO GOVERNMENT GRANTS

The present invention was supported by funds from the U.S. Government (NIH Grant No. IK08A1085033) and the U.S. Government may therefore have certain rights in the invention.

FIELD OF THE INVENTION

The present invention is directed, in part, to compounds or pharmaceutically acceptable salts thereof, for treating tuberculosis.

BACKGROUND OF THE INVENTION

The problem of tuberculosis continues to take a tremendous toll on global health, accounting for almost 2 million deaths per year, despite the discovery of antitubercular chemotherapy more than half a century ago. In fact, the crisis is growing due to the alarming increase in multi-drug resistant, and even totally-drug resistant strains, coupled with the extremely little progress made in discovering new TB drugs. One of the major barriers to discovering new, potentially more effective agents has been the lack of a fundamental understanding of the physiology of the *M. tuberculosis bacilli* as they exist within the infected human host. This physiology contributes to their ability to survive for decades within an infected individual despite host immunity, and to persist even in the face of what should otherwise be effective chemotherapy thus dictating the extremely long treatment courses that are required for cure. Accordingly, there is a need for new compounds and therapeutics for treating tuberculosis. The present disclosure fulfills these needs as well as others.

SUMMARY OF THE INVENTION

In some embodiments, compounds described herein are provided. In some embodiments, the compound is a compound of Formula I or a pharmaceutically acceptable salt, ester or prodrug thereof:

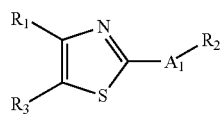

I wherein:
$A_1$ is $NR_{18}$, O, or S, $(CH_2)_q$, or $-NH(CH_2)_q'$, $-N(H)-N=C^*-(CH_2)_mCH_3$ $R_1$ is optionally substituted alkyl, optionally substituted aryl, optionally substituted pyridyl, optionally substituted pyrimidinyl, optionally substituted pyrazinyl, optionally substituted pyridazinyl, or triazinyl; dd-dd $R_2$ is, optionally substituted aryl, optionally substituted pyridyl, optionally substituted pyritnidinyl, optionally substituted pyrazinyl, optionally substituted pyridazinyl, or triazinyl;

$R_3$ is H, $OR_4$, $NR_5R_6$, $NO_2$, $SO_2NH_2$, halo, optionally substituted alkyl, optionally substituted heteroalkyl, optionally substituted aryl, optionally substituted heteroaryl, optionally substituted carbocycle, optionally substituted heterocycle, optionally substituted carboxyl, optionally substituted alkoxycarbony), or optionally substituted aryloxycarbonyl;

$R_4$, $R_5$, and $R_6$ are each independently H, halo, optionally substituted alkyl, optionally substituted heteroalkyl, optionally substituted aryl, optionally substituted hetcroary), optionally substituted carbocycle, or optionally substituted heterocycle;

$R_{18}$ is H, optionally substituted alkyl, optionally substituted aryl, optionally substituted arylalkyl, optionally substituted heteroaryl, optionally substituted carbocycle, or optionally substituted heterocycle;

C* is where $R_2$ bonds with the group $-N(H)-N=C^*-(CH_2)_mCH_3$;

m is 0-6; and q is 1-6.

In some embodiments, pharmaceutical compositions comprising a compound described herein, or a pharmaceutically acceptable salt, ester or prodrug thereof is provided.

In some embodiments, methods of treating tuberculosis are provided, in some embodiments, the methods of treating tuberculosis comprise administering to a subject a compound described herein, or a pharmaceutically acceptable salt, ester or prodrug thereof, or a pharmaceutical composition described herein. In some embodiments, the tuberculosis is replicating tuberculosis. In some embodiments, the tuberculosis is non-replicating.

DESCRIPTION OF EMBODIMENTS

Unless defined otherwise, all technical and scientific terms have the same meaning as is commonly understood by one of ordinary skill in the an to which the embodiments disclosed belongs.

As used herein, the terms "a" or "an" means that "at least one" or "one or more" unless the context clearly indicates otherwise.

As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

As used herein, the terms "IC90" or "IC99" when used as reference to a non-replicating population of *M. tuberculosis* is the inhibitory concentration of a compound(s) or composition(s) that results in 90% or 99% killing of the non-replicating population of *M. tuberculosis*, respectively. As used herein, the terms "IC90" or "IC99" when used as reference to a replicating population of *M. tuberculosis* is the "inhibitory concentration" that results in 90% or 99% growth inhibition of a replicating population of *M. tuberculosis*.

As used herein, the term "alkenyl" means a straight or branched alkyl group having one or more double carbon-carbon bonds and 2-20 carbon atoms, including, but not limited to, ethenyl, 1-propenyl, 2-propenyl, 2-methyl-1-propenyl, 1-butenyl, 2-butenyl, and the like. In some embodiments, the alkenyl chain is from 2 to 10 carbon atoms in length, from 2 to 8 carbon atoms in length, from 2 to 6 carbon atoms in length, or from 2 to 4 carbon atoms in length.

The terms "alkoxy", "phenyloxy", "benzoxy" and "pyrimidinyloxy" refer to an alkyl group, phenyl group, benzyl group, or pyrimidinyl group, respectively, each optionally substituted, that is bonded through an oxygen atom. For example, the term "alkoxy" means a straight or branched —O-alkyl group of 1 to 20 carbon atoms, including, but not limited to, methoxy, ethoxy, n-propoxy, isopropoxy, t-butoxy, and the like. In some embodiments, the alkoxy chain is from 1 to 10 carbon atoms in length, from 1 to 8 carbon atoms in length, from 1 to 6 carbon atoms in length, from 1 to 4 carbon atoms in length, from 2 to 10 carbon atoms in length, from 2 to 8 carbon atoms in length, from 2 to 6 carbon atoms in length, or from 2 to 4 carbon atoms in length.

As used herein, the term "alkyl" means a saturated hydrocarbon group which is straight-chained or branched. An alkyl group can contain from 1 to 20, from 2 to 20, from 1 to 10, from 2 to 10, from 1 to 8, from 2 to 8, from 1 to 6, from 2 to 6, from 1 to 4, from 2 to 4, from 1 to 3, or 2 or 3 carbon atoms. Examples of alkyl groups include, but are not limited to, methyl (Me), ethyl (Et), propyl (e.g., n-propyl and isopropyl), butyl (e.g., n-butyl, t-butyl, isobutyl), pentyl (e.g., n-pentyl, isopentyl, neopentyl), hexyl, isohexyl, heptyl, 4,4-dimethylpentyl octyl, 2,2,4-trimethylpentyl, nonyl, decyl, undecyl, dodecyl, 2-methyl-1-propyl, 2-methyl-2-propyl, 2-methyl-1-butyl, 3-methyl-1-butyl, 2-methyl-3-butyl, 2-methyl-1-pentyl, 2,2-dimethyl-1-propyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, and the like.

As used herein, the term "alkylamino" means an amino group substituted by an alkyl group having from 1 to 6 carbon atoms. An example of an alky lamino is $—NHCH_2CH_3$.

As used herein, the term "alkylene" or "alkylenyl" means a divalent alkyl linking group. An example of an alkylene (or alkylenyl) is methylene or methylenyl ($—CH_2—$).

As used herein, the term "alkylthio" means an —S-alkyl group having from 1 to 6 carbon atoms. An example of an alkylthio group is $—SCH_2CH_3$.

As used herein, the term "alkynyl" means a straight, or branched alkyl group having one or more triple carbon-carbon bonds and 2-20 carbon atoms, including, but not limited to, acetylene, 1-propylene, 2-propylene, and the like. In some embodiments, the alkynyl chain is 2 to 10 carbon atoms in length, from 2 to 8 carbon atoms in length, from 2 to 6 carbon atoms in length, or from 2 to 4 carbon atoms in length.

As used herein, the term "amidino" means $—C(=NH)NH_2$.

As used herein, the term "amino" means $—NH_2$.

As used herein, the term "aminoalkoxy" means an alkoxy group substituted by an amino group. An example of an aminoalkoxy is $—OCH_2CH_2NH_2$.

As used herein, the term "aminoalkyl" means an alkyl group substituted by an amino group. An example of an aminoalkyl is $—CH_2CH_2NH_2$.

As used herein, the term "aminosulfonyl" means $—S(=O)_2NH_2$.

As used herein, the term "aminoalkylthio" means an alkylthio group substituted by an amino group. An example of an aminoalkylthio is $—SCH_2CH_2NH_2$.

As used herein, the term "animal" includes, but is not limited to, humans and non-human vertebrates such as wild, domestic, and farm animals.

As used herein, the term "aryl" means a monocyclic, bicyclic, or polycyclic (e.g., having 2, 3 or 4 fused rings) aromatic hydrocarbons. In some embodiments, aryl groups have from 6 to 20 carbon atoms or from 6 to 10 carbon atoms. Examples of aryl groups include, but are not limited to, phenyl, naphthyl, anthracenyl, phenanthrenyl, indanyl, indenyl tetrahydronaphthyl, and the like. Examples of aryl groups include, but are not limited to:

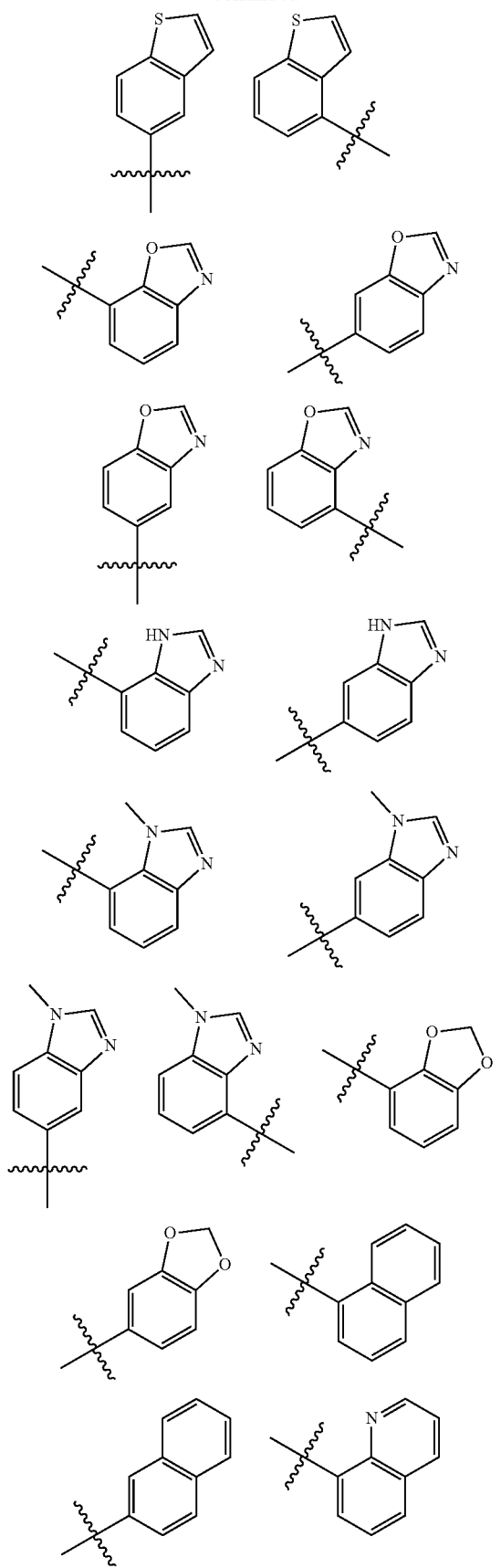
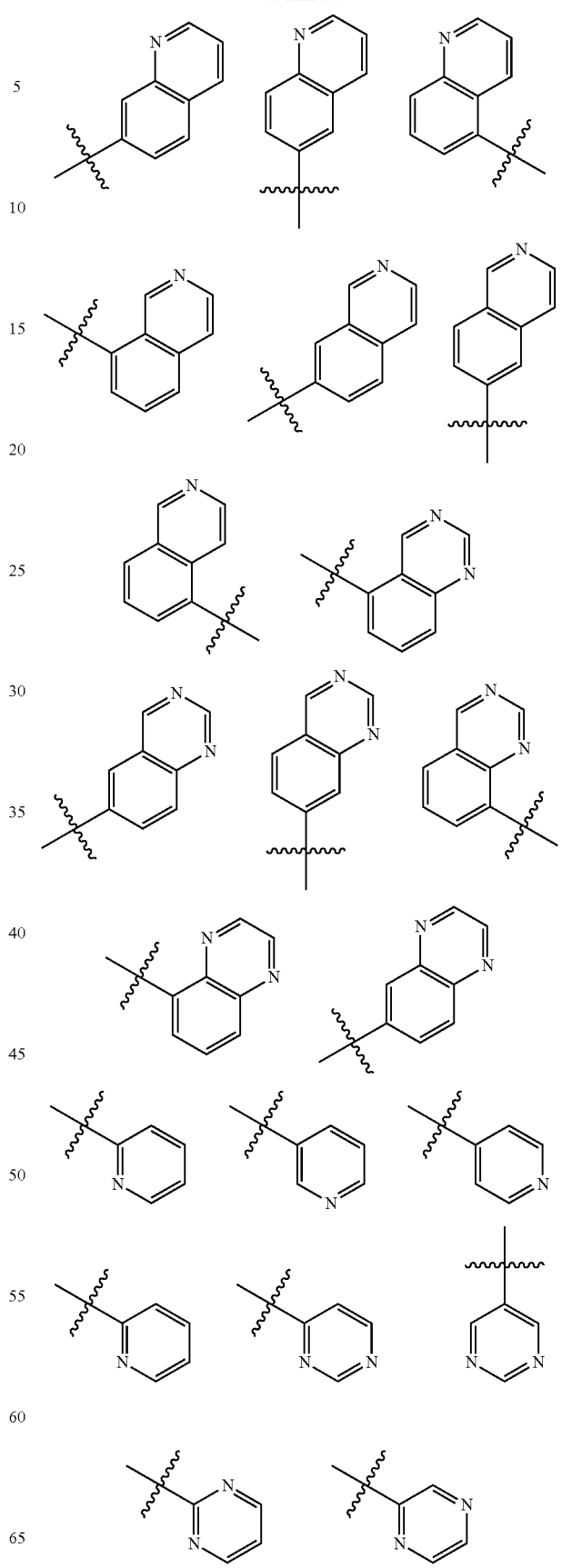

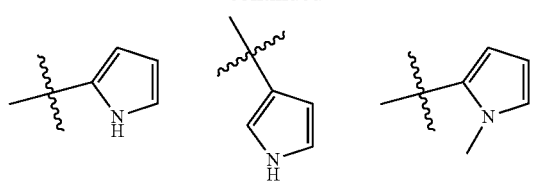
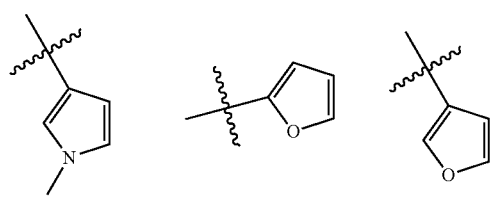
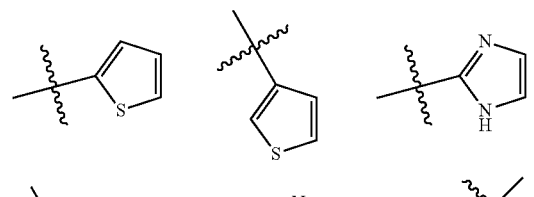
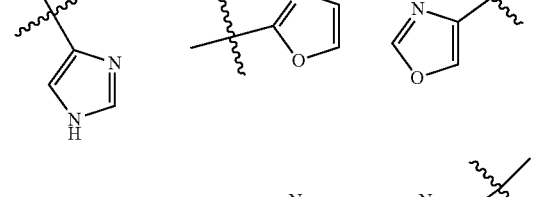
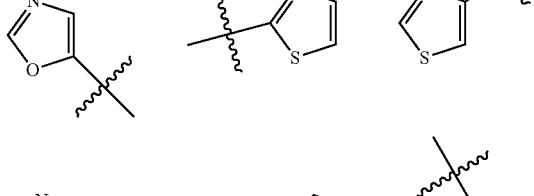
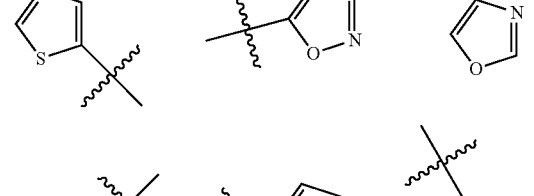
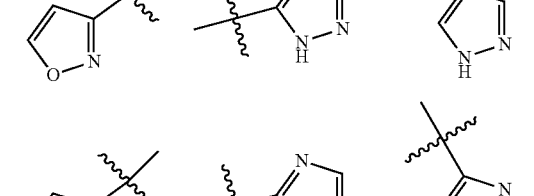
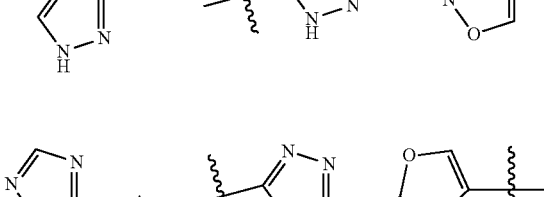
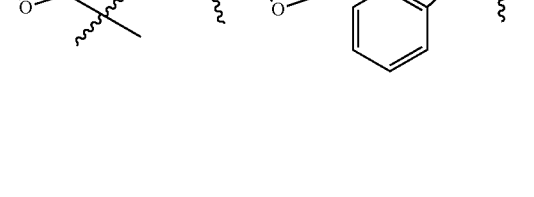
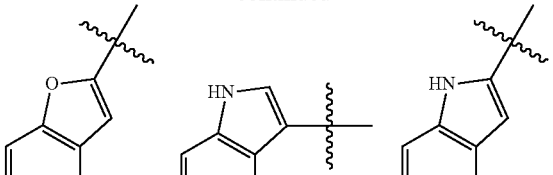
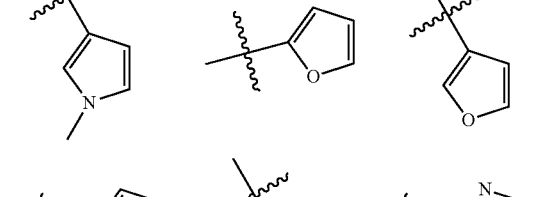
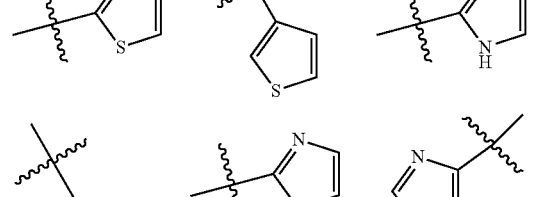
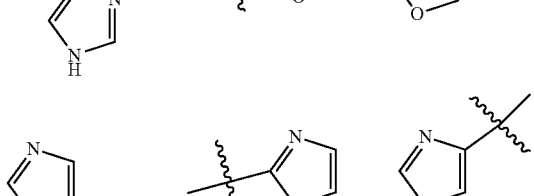
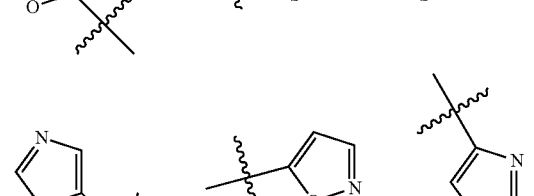
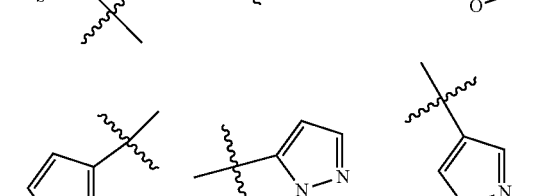
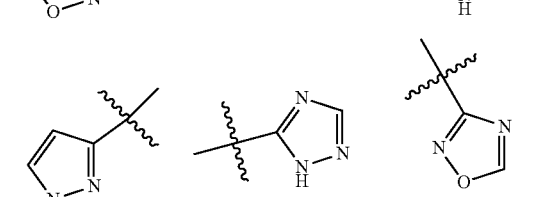
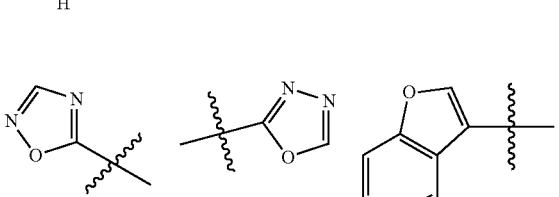

As used herein, the term "arylalkyl" means a $C_{1-6}$ alkyl substituted by aryl.

As used herein, the term "arylamino" means an amino group substituted by an aryl group. An example of an arylamino is —NH(phenyl).

As used herein, the term "arylene" means an aryl linking group, i.e., an aryl group that links one group to another group in a molecule.

As used herein, the "carbamoyl" means —C(=O)—NH$_2$.

As used herein, the term "carbocycle" means a 5- or 6-membered, saturated or unsaturated cyclic ring, optionally containing O, S, or N atoms as pan of the ring. Examples of carbocycles include, but are not limited to, cyclopentyl, cyclohexyl, cyclopenta-1,3-diene, phenyl, and any of the hetcrocyeies recited above.

As used herein, the term "carrier" means a diluent, adjuvant, or excipient with which a compound is administered. Pharmaceutical carriers can be liquids, such as water and oils, including those of petroleum, animal, vegetable or synthetic origin, such as peanut oil, soybean oil, mineral oil, sesame oil and the like. The pharmaceutical carriers can also be saline, gum acacia, gelatin, starch paste, talc, keratin, colloidal silica, urea, and the like. In addition, auxiliary, stabilizing, thickening, lubricating and coloring agents can be used.

As used herein, the term, "compound" means all stereoisomers, tautomers, and isotopes of the compounds described herein.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, unrecited elements or method steps.

As used herein, the term "contacting" means bringing together of two elements in an in vitro system or an in vivo system.

As used herein, the term "cyano" means —CN.

As used herein, the term "cycloalkyl" means non-aromatie cyclic hydrocarbons including cvclized alkyl, alkenyl, and alkynyl groups that contain up to 20 ring-forming carbon atoms. Cycloalkyl groups can include mono- or polycyclic ring systems such as fused ring systems, bridged ring systems, and spiro ring systems. In some embodiments, polycyclic ring systems include 2, 3, or 4 fused rings. A cycloalkyl group can contain from 3 to 15, from 3 to 10, from 3 to 8, from 3 to 6, from 4 to 6, from 3 to 5, or 5 or 6 ring-forming carbon atoms. Ring-forming carbon atoms of a cycloalkyl group can be optionally substituted by oxo or sulfide. Examples of cycloalkyl groups include, but are not limited to, cyclopropyl, cyclobutyl, cyclopentyl, cyclohexyl, cycloheptyl, cyclooctyl, cyclononyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (having a bond in common with) to the cycloalkyl ring, for example, benzo or thienyl derivatives of pentane, pentene, hexane, and the like (e.g., 2,3-dihydro-1H-indene-1-yl, or 1H-inden-2(3H)-one-1-yl).

As used herein, the term "cycloalkylalkyl" means a $C_{1-6}$ alkyl substituted by cycloalkyl.

As used herein, the term "dialkylamino" means an amino group substituted by two alkyl groups, each having from 1 to 6 carbon atoms.

As used herein, the term "diazamino" means —$N(NH_2)_2$.

As used herein, the term "guanidino" means —NH(=NH)$NH_2$.

As used herein, the term "halo" means halogen groups including, but not limited to fluoro, chloro, bromo, and iodo.

As used herein, the term "haloalkoxy" means an —O-haloalkyl group. An example of an haloalkoxy group is $OCF_3$.

As used herein, the term "haloalkyl" means a $C_{1-6}$ alkyl group having one or more halogen substituents. Examples of haloalkyl groups include, but are not limited to, $CF_3$, $C_2F_5$, $CHF_2$, $CCl_3$, $CHCl_2$, $C_2Cl_5$, $CH_2CF_3$, and the like.

As used herein, the term "heteroaryl" means an aromatic heterocycle having up to 20 ring-forming atoms (e.g., C) and having at least one heteroatom ring member (ring-forming atom) such as sulfur, oxygen, or nitrogen. In some embodiments, the heteroaryl group has at least one or more heteroatom ring-forming atoms, each of which are, independently, sulfur, oxygen, or nitrogen. In some embodiments, the heteroaryl group has from 3 to 20 ring-forming atoms, from 3 to 10 ring-forming atoms, from 3 to 6 ring-forming atoms, or from 3 to 5 ring-forming atoms. In some embodiments, the heteroaryl group contains 2 to 14 carbon atoms, from 2 to 7 carbon atoms, or 5 or 6 carbon atoms. In some embodiments, the heteroaryl group has 1 to 4 heteroatoms, 1 to 3 heteroatoms, or 1 or 2 heteroatoms. Heteroaryl groups include monocyclic and polycyclic (e.g., having 2, 3 or 4 fused rings) systems. Examples of heteroaryl groups include, but are not limited to, pyridyl, pyrimidinyl, pyrazinyl, pyridazinyl, triazinyl, furyl, quinolyl, isoquinolyl, thienyl, imidazolyl, thiazoiyl, indolyl (such as indol-3-yl), pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, pyranyl, oxadiazolyl, isoxazolyl, triazolyl, thianthrenyl, pyrazolyl, indolizinyl, isoindolyl, isobenzofuranyl, benzoxazolyl, xanthenyl, 2H-pyrrolyl, pyrrolyl, 3H-indolyl, 4H-quinolizinyl, phthalazinyl, naphthyridinyl, quinazolinyl, phenanthridinyl, acridinyl, perimidinyl, phenanthrolinyl, phenazinyl, isothiazolyl, phenothiazinyl, isoxazolyl, furazanyl, phenoxazinyl groups, and the like. Suitable heteroaryl groups include 1,2,3-triazole, 1,2,4-triazole, 5-amino-1,2,4-triazole, imidazole, oxazole, isoxazole, 1,2,3-oxadiazole, 1,2,4-oxadiazole, 3-amino-1,2,4-oxadiazole, 1,2,5-oxadiazole, 1,3,4-oxadiazole, pyridine, and 2-aminopyridine.

As used herein, the term "heteroarylalkyl" means a $C_{1-6}$ alkyl group substituted by a heteroaryl group.

As used herein, the term "heteroarylamino" means an amino group substituted by a heteroaryl group. An example of a heteroarylamino is —NH—(2-pyridyl).

As used herein, the term "heteroarylene" means a heteroaryl linking group, i.e., a heteroaryl group that links one group to another group in a molecule.

As used herein, the term "heterocycle" or "heterocyclic ring" means a 5- to 7-membered mono- or bicyclic or 7- to 10-membered bicyclic heterocyclic ring system any ring of which may be saturated or unsaturated, and which consists of carbon atoms and from one to three heteroatoms chosen from N, O and S, and wherein the N and S heteroatoms may optionally be oxidized, and the N heteroatom may optionally be quaternized, and including any bicyclic group in which any of the above-defined heterocyclic rings is fused to a benzene ring. Particularly useful are rings containing one oxygen or sulfur, one to three nitrogen atoms, or one oxygen or sulfur combined with one or two nitrogen atoms. The heterocyclic ring may be attached at any heteroatom or carbon atom which results in the creation of a stable structure. Examples of heterocyclic groups include, but are not limited to, piperidynyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolklinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, bonzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl.

As used herein, the term "heterocycloalkyl" means non-aromatic heterocycles having up to 20 ring-forming atoms including cyclized alkyl, alkenyl, and alkynyl groups, where one or more of the ring-forming carbon atoms is replaced by a heteroatom such as an O, N, or S atom. Heterocyeloalkyl groups can be mono or polycyclic (e.g., fused, bridged, or spiro systems). In some embodiments, the heterocyeloalkyl group has from 1 to 20 carbon atoms, or from 3 to 2.0 carbon atoms. In some embodiments, the heterocyeloalkyl group contains 3 to 14 ring-forming atoms, 3 to 7 ring-forming atoms, or 5 or 6 ring-forming atoms. In some embodiments, the heterocyeloalkyl group has 1 to 4 heteroatoms, 1 to 3 heteroatoms, or 1 or 2 heteroatoms. In some embodiments, the heterocyeloalkyl group contains 0 to 3 double bonds. In some embodiments, the heterocyeloalkyl group contains 0 to 2 triple bonds. Examples of heterocyeloalkyl groups include, but are not limited to, morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, oxazolidinyl, isothiazolidinyl, pyrazolidinyl, thiazolidinyl, iraidazolidinyl, pyrrolidin-2-one-3-yl, and the like. In addition, ring-forming carbon atoms and heteroatoms of a heterocyeloalkyl group can be optionally substituted by oxo or sulfido. For example, a ring-forming S atom can be substituted by 1 or 2 oxo (form a S(O) or S(O)$_2$). For another example, a ring-forming C atom can be substituted by oxo (form carbonyl). Also included in the definition of heterocyeloalkyl are moieties that have one or more aromatic rings fused (having a bond in common with) to the nonaromatic heterocyclic ring including, but not limited to, pyridinyl, thiophenyl, phthalimidyl, naphthalimidyl, and benzo derivatives of heterocycles such as indolene, isoindoiene, 4,5,6,7-tetrahydrothieno[2,3-c]pyridine-5-yl, 5,6-dihydrothieno[2,3-c]pyridin-7(4H)-one-5-yl, isoindoin-1-one-3-yl, and 3,4-dihydroisoquinolin-1(2H )-one-3yl groups. Ring-forming carbon atoms and heteroatoms of the heterocyeloalkyl group can be optionally substituted by oxo or sulfido.

As used herein, the term "heterocycloalkylalkyl" refers to a $C_{1-6}$alkyl substituted by heterocyeloalkyl.

As used herein, the term "hydoxy" or "hydroxyl" means an —OH group.

As used herein, the term "hydroxyalkyl" or "hydroxylalkyl" means an alkyl group substituted by a hydroxyl group. Examples of a hydroxylalkyl include, but are nut limited to, —CH$_2$OH and —CH$_2$CH$_2$OH.

As used herein, the term "individual" or "patient," used interchangeably, means any animal, including mammals, such as mice, rats, other rodents, rabbits, dogs, cats, swine, cattle, sheep, horses, or primates, such as humans. The individual can also be referred to as a subject.

As used herein, the phrase "in need thereof" means that the animal or mammal has been identified as having a need for the particular method or treatment. In some embodiments, the identification can be by any means of diagnosis. In any of the methods and treatments described herein, the animal or mammal can be in need thereof. In some embodiments, the animal or mammal is in an environment or will be traveling to an environment in which a particular disease, disorder, or condition is prevalent.

As used herein, the phrase "integer from X to Y" means any integer that includes the endpoints. For example, the phrase "integer from X to Y" means 1, 2, 3, 4, or 5.

As used herein, the term "isolated" means that the compounds described herein are separated from other components of either (a) a natural source, such as a plant or cell, or (b) a synthetic organic chemical reaction mixture, such as by conventional techniques.

As used herein, the term "mammal" means a rodent (i.e., a mouse, a rat, or a guinea pig), a monkey, a cat, a dog, a cow, a horse, a pig, or a human. In some embodiments, the mammal is a human.

As used herein, the term "nitro" means —NO$_2$.

As used herein, the term "n-membered", where n is an integer, typically describes the number of ring-forming atoms in a moiety, where the number of ring-forming atoms is n. For example, pyridine is an example of a 6-membered heteroaryl ring and thiophene is an example of a 5-membered heteroaryl ring.

As used herein, the phrase "optionally substituted" means that substitution is optional and therefore includes both unsubstituted and substituted atoms and moieties. A "substituted" atom or moiety indicates that any hydrogen on the designated atom or moiety can be replaced with a selection from the indicated substituent groups, provided that the normal valency of the designated atom or moiety is not exceeded, and that the substitution results in a stable compound. For example, if a methyl group is optionally substituted, then 3 hydrogen atoms on the carbon atom can be replaced with substituent groups.

As used herein, the phrase "pharmaceutically acceptable" means those compounds, materials, compositions, and/or dosage forms which are, within the scope of sound medical judgment, suitable for use in contact with tissues of humans and animals. In some embodiments, "pharmaceutically acceptable" means approved by a regulatory agency of the Federal or a state government or listed in the U.S. Pharmacopeia or other generally recognized pharmacopeia tor use in animals, and more particularly in humans.

As used herein, the phrase "pharmaceutically acceptable salt(s)," includes, but is not limited to, salts of acidic or basic groups. Compounds that are basic in nature are capable of forming a wide variety of salts with various inorganic and organic acids. Acids that may be used to prepare pharmaceutically acceptable acid addition salts of such basic compounds are those that form non-toxic acid addition salts, i.e., salts containing pharmacologically acceptable anions including, but not limited to, sulfuric, thiosulfuric, citric, maleic, acetic, oxalic, hydrochloride, hydrobromide, hydroiodide, nitrate, sulfate, bisulfate, bisulfite, phosphate, acid phosphate, isonicotinate, borate, acetate, lactate, salicylate, citrate, acid citrate, tartrate, oleate, tannate, pantothenate, bitartrate, ascorbate, succinate, maleate, gentismate, fumarate, gluconate, glucaronate, saccharate, formate, benzoate, glutamate, methanesulfonate, ethanesulfonate, benzenesulfonate, p-toluensulfonate, bicarbonate, malonate, mesylate, esylate, napsydisyfate, tosylate, besylate, orthophoshate, trifluoroacetate, and pamoate (i.e., 1,1'-methylene-bis-(2-hydroxy-3-naphthoate)) salts. Compounds that include an amino moiety may form pharmaceutically acceptable salts with various amino acids, in addition to the acids mentioned above. Compounds that are acidic in nature are capable of forming base salts with various pharmacologically acceptable cations. Examples of such salts include, but are not limited to, alkali metal or alkaline earth metal salts and, particularly, calcium, magnesium, ammonium, sodium, lithium, zinc, potassium, and iron sails. The present invention also includes quaternary ammonium salts of the compounds described herein, where the compounds have one or more tertiary amine moiety.

As used herein, the term "phenyl" means —$C_6H_5$. A phenyl group can be unsubstituted or substituted with one, two, or three suitable substituents.

As used herein, the terms "prevention" or "preventing" mean a reduction of the risk of acquiring a particular disease, condition, or disorder.

As used herein, the term "prodrug" means a derivative of a known direct acting drug, which derivative has enhanced delivery characteristics and therapeutic value as compared to the drug, and is transformed into the active drug by an enzymatic or chemical process.

As used herein, the term "purified" means that when isolated, the isolate contains at least 90%, at least 95%, at least 98%, or at least 99% of a compound described herein by weight of the isolate.

As used herein, the phrase "substantially isolated" means a compound that is at least partially or substantially separated from the environment in which it is formed or detected.

As used herein, the phrase "suitable substituent" or "substituent" means a group that does not nullify the synthetic or pharmaceutical utility of the compounds described herein or the intermediates useful for preparing them. Examples of suitable substituents include, but are not limited to: $C_1$-$C_6$alkyl, $C_1$-$C_6$alkenyl, $C_1$-$C_6$alkynyl, $C_5$-$C_6$aryl, $C_1$-$C_6$alkoxy, $C_3$-$C_5$heteroaryl, $C_3$-$C_6$cycloalkyl, $C_5$-$C_6$aryloxy, —CN, —OH, oxo, halo, haloalkyl, —$NO_2$, —$CO_2H$, —$NH_2$, —NH($C_1$-$C_8$alkyl), —N($C_1$-$C_3$alkyl)$_2$, —NH($C_6$aryl), —N($C_5$-$C_6$)$_2$), —CHO, —CO($C_1$-$C_6$alkyl), —CO(($C_5$-$C_6$)aryl), —$CO_2$(($C_1$-$C_6$)alkyl), and —$CO_2$(($C_5$-$C_6$)aryl). One of skill in art can readily choose a suitable substituent based on the stability and pharmacological and synthetic activity of the compounds described herein.

As used herein, the phrase "therapeutically effective amount" means the amount of active compound or pharmaceutical agent that elicits the biological or medicinal response that is being sought in a tissue, system, animal, individual or human by a researcher, veterinarian, medical doctor or other clinician. The therapeutic effect is dependent upon the disorder being treated or the biological effect desired. As such, the therapeutic effect can be a decrease in the severity of symptoms associated with the disorder and/or inhibition (partial or complete) of progression of the disorder, or improved treatment, healing, prevention or elimination of a disorder, or side effects. The amount needed to elicit the therapeutic response can be determined based on the age, health, size and sex of the subject. Optimal amounts can also be determined based on monitoring of the subject's response to treatment.

As used herein, the terms "treat," "treated," or "treating" mean both therapeutic treatment and prophylactic or preventative measures wherein the object is to prevent or slow down (lessen) an undesired physiological condition, disorder or disease, or obtain beneficial or desired clinical results. Beneficial or desired clinical results include, but are not limited to, alleviation of symptoms; diminishment of extent of condition, disorder or disease; stabilized (i.e., not worsening) state of condition, disorder or disease; delay in onset or slowing of condition, disorder or disease progression; amelioration of the condition, disorder or disease state or remission (whether partial or total), whether detectable or undetectable; an amelioration of at least one measurable physical parameter, not necessarily discernible by the patient; or enhancement or improvement of condition, disorder or disease. Treatment includes eliciting a clinically significant response without excessive levels of side effects. Treatment also includes prolonging survival as compared to expected survival if not receiving treatment. Thus, "treatment of tuberculosis" or "treating tuberculosis" means an activity that prevents, alleviates or ameliorates any of the primary phenomena (initiation, progression, metastasis) or secondary symptoms associated with the tuberculosis. As used herein, the phrase "treating tuberculosis" or "treatment of tuberculosis" also refers to the treatment of a subject infected with M. tuberculosis bacilli. The treatment can target replicating M. tuberculosis bacilli and/or non-replicating M. tuberculosis bacilli. In some embodiments, the compounds can selectively target one form (e.g. non-replicating or replicating) of M. tuberculosis bacilli.

At various places in the present specification, substituents of compounds may be disclosed in groups or in ranges. It is specifically intended that embodiments include each and every individual subcombination of the members of such groups and ranges. For example, the term "$C_{1-6}$alkyl" is specifically intended to individually disclose methyl, ethyl, propyl, $C_4$alkyl, $C_5$alkyl, and $C_6$alkyl.

For compounds in which a variable appears more than once, each variable can be a different moiety selected from the Markush group defining the variable. For example, where a structure is described having two R groups that are simultaneously present on the same compound, the two R groups can represent different moieties selected from the Markush groups defined for R. In another example, when an optionally multiple substituent is designated in the form, for example,

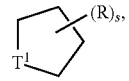

then it is understood that substituent R can occur s number of times on the ring, and R can be a different moiety at each occurrence. Further, in the above example, where the variable $T^1$ is defined to include hydrogens, such as when $T^1$ is $CH_2$, NH, etc., any H can be replaced with a substituent.

It is further appreciated that certain features described herein, which are, for clarity, described in the context of separate embodiments, can also be provided in combination in a single embodiment. Conversely, various features which are for brevity, described in the context of a single embodiment, can also be provided separately or in any suitable subcombination.

It is understood that the present invention encompasses the use, where applicable, of stereoisomers, diastercomers and optical stereoisomers of the compounds of the invention, as well as mixtures thereof. Additionally, it is understood that stereoisomers, diastercomers, and optical stereoisomers of the compounds of the invention, and mixtures thereof, are within the scope of the invention. By way of non-limiting example, the mixture may be a raceroate or the mixture may comprise unequal proportions of one particular stereoisomer over the other. Additionally, the compounds can be provided as substantially pure stereoisomers, diastercomers and optical stereoisomers (such as epimers).

The compounds described herein can be asymmetric (e.g., having one or more stereocenters). All stereoisomers, such as enantiomers and diastercomers, are intended to be included within the scope of the invention unless otherwise indicated. Compounds that contain asymmetrically substituted carbon atoms can be isolated in optically active or racemic forms. Methods of preparation of optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds are also included within the scope of the invention and can be isolated as a mixture of isomers or as separated isomeric forms. Where a compound capable of stereoisomerism or geometric isomerism is designated in its structure or name without reference to specific R/S or cis/trans configurations, it is intended that all such isomers are contemplated.

Resolution of racemic mixtures of compounds can be carried out by any of numerous methods known in the art, including, for example, fractional recrystallization using a chiral resolving acid which is an optically active, salt-forming organic acid. Suitable resolving agents for fractional recrystallizaiion methods include, but are not limited to, optically active acids, such as the D and L forms of tartaric acid, diacetyltartaric acid, dibenzoyltartaric acid, mandelic acid, malic acid, lactic acid, and the various optically active amphorsulfonic acids such as β-camphorsulfonic acid. Other resolving agents suitable for fractional crystallization methods include, but are not limited to, stereoisomcrically pure forms of α-methytbenzylamine (e.g., S and R forms, or diastereomerically pure forms), 2-phenylglycinol, norephedrine, ephedrine, N-methylephedrine, cyclohexyltethylamine. 1,2-diaminocyclohexane, and the like. Resolution of racemic mixtures can also be carried out by elution on a column packed with an optically active resolving agent (e.g., dinitrobenzoylphenylglycine). Suitable elution solvent compositions can be determined by one skilled in the art.

Compounds may also include tautomeric forms. Tautomeric forms result from the swapping of a single bond with an ad jacent double bond together with the concomitant migration of a proton. Tautomeric forms include prototropic taufomers which are isomeric protonation states having the same empirical formula and total charge. Examples of prototropic tautomers include, but are not limited to, kelone-enol pairs, amide-imidic acid pairs, lactam-lactim pairs, amide-imidic acid pairs, enamine-irame pairs, and annular forms where a proton can occupy two or more positions of a heterocyclic system including, but not limited to, 1H- and 3H-imidazole, 1H-, 2H- and 4H-1,2,4-triazole, 1H- and 2H-isomdole, and 1H- and 2H-pyrazole. Tautomeric forms can be in equilibrium or sterically locked into one form by appropriate substitution.

Compounds also include hydrates and solvates, as well as anhydrous and non-solvated forms.

Compounds can also include all isotopes of atoms occurring in the intermediates or final compounds. Isotopes include those atoms having the same atomic number but different mass numbers. For example, isotopes of hydrogen include tritium and deuterium.

In some embodiments, the compounds, or salts thereof, are substantially isolated. Partial separation can include, for example, a composition enriched in the compound of the invention. Substantial separation can include compositions containing at least, about 50%, at least about 60%, at least about 70%, at least about 80%, at least about 90%, at least about 95%, at least about 97%, or at least about 99% by weight of the compound of the invention, or salt thereof. Methods for isolating compounds and their salts are routine in the art.

Although the disclosed compounds are suitable, other functional groups can be incorporated into the compound with an expectation of similar results. In particular, thioamides and thioestcrs are anticipated to have very similar properties. The distance between aromatic rings can impact the geometrical pattern of the compound and this distance can be altered by incorporating aliphatic chains of varying length, which can be optionally substituted or can comprise an amino acid, a dicarboxylic acid or a diamine. The distance between and the relative orientation of monomers within the compounds can also be altered by replacing the amide bond with a surrogate having additional atoms. Thus, replacing a carbonyl group with a dicarbonyl alters the distance between the monomers and the propensity of dicarbonyl unit to adopt an anti-arrangement of the two carbonyl moiety and alter the periodicity of the compound. Pyromeliitic anhydride represents still another alternative to simple amide linkages which can alter the conformation and physical properties of the compound. Modern methods of solid phase organic chemistry (E. Atherton and R. C. Sheppard, Solid Phase Peptide Synthesis A Practical Approach IRL Press Oxford 1989) now allow the synthesis of homodisperse compounds with molecular weights approaching 5,000 Daltons. Other substitution patterns are equally effective.

The compounds also include derivatives referred to as prodrags.

Compounds containing an amine function can also form N-oxides. A reference herein to a compound that contains an amine function also includes the N-oxide. Where a compound contains several amine functions, one or more than one nitrogen atom can be oxidized to form an N-oxide. Examples of N-oxides include N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g., a pcroxycarboxylic acid) (see. Advanced Organic Chemistry, by Jerry March, 4th Edition, Wiley Interscience).

Embodiments of various compounds and salts thereof are provided. Where a variable is not specifically recited, the variable can be any option described herein, except as otherwise noted or dictated by context.

In some embodiments, a compound of Formula I or a pharmaceutically acceptable salt, ester or prodrug thereof is provided:

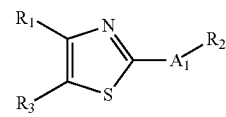

I wherein:

$A_1$ is $NR_{18}$, O, or S, $(CH_2)_q$, or —$NH(CH_2)_q'$, —N(H)—N=C*—$(CH_2)_mCH_3$ $R_1$ is optionally substituted alkyl optionally substituted aryl, optionally substituted pyridyl, optionally substituted pyrimidinyl optionally substituted pyrazinyl optionally substituted pyridazinyl or triazinyl;

$R_2$ is, optionally substituted aryl, optionally substituted pyridyl optionally substituted pyrimidinyl, optionally substituted pyrazinyl optionally substituted pyridazinyl or triazinyl;

$R_3$ is H, $OR_4$, $NR_5R_6$, $NO_2$, $SO_2NH_2$, halo, optionally substituted alkyl optionally substituted heteroalkyl optionally substituted aryl, optionally substituted heteroaryl, optionally substituted carbocycle, optionally substituted heterocycle, optionally substituted carboxyl optionally substituted alkoxycarbonyl or optionally substituted aryloxycarbonyl;

$R_4$, $R_5$, and $R_6$ are each independently H, halo, optionally substituted alkyl optionally substituted heteroalkyl optionally substituted aryl, optionally substituted heteroaryl optionally substituted carbocycle, or optionally substituted heterocycle;

$R_{18}$ is H, optionally substituted alkyl, optionally substituted aryl, optionally substituted arylalkyl, optionally substituted heteroaryl, optionally substituted carbocycle, or optionally substituted heterocycle;

C* is where $R_2$ bonds with the group —N(H)—N=C*—$(CH_2)_m CH_3$;

m is 0-6; and q is 1-6.

In some embodiments, $A_1$ is $NR_{18}$. In some embodiments, $A_1$ is O. In some embodiments, $A_1$ is S. In some embodiments, $A_1$ is $(CH_2)_q$, wherein q is 1-6. In some embodiments, $A_1$ is $NH(CH_2)_q$, wherein q is 1-6. In some embodiments, $A_1$ is —N(H)—N=C*—$(CH_2)_m CH_3$, wherein m is 0-6. The C* denotes the carbon where the R group, such as $R_2$, binds to the substituent that contains the C*.

In some embodiments, R is H, halo, or optionally substituted $C_1$-$C_6$ alkyl. In some embodiments, $R_3$ is $OR_4$, $NR_5R_6$, $NO_2$, or $SO_2NH_2$. In some embodiments $R_3$ is optionally substituted heteroalkyl optionally substituted aryl, optionally substituted heteroaryl. optionally substituted carbocycle, or optionally substituted heterocycle. In some embodiments, $R_3$ is optionally substituted carboxyl, optionally substituted alkoxycarbonyl, or optionally substituted aryloxycarbonyl.

In some embodiments, $R_1$ is:

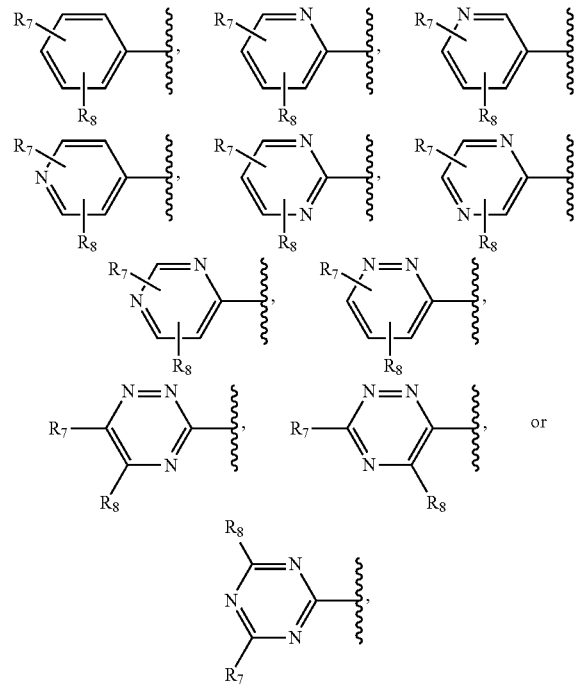

wherein:

$R_7$ and $R_8$ are each independently H, $OR_{11}$, $NR_{12}R_{13}$, $NO_2$, $SO_2NH_2$, halo, optionally substituted alkyl, optionally substituted heteroalkyl, optionally substituted aryl, optionally substituted heteroaryl, optionally substituted carbocycle, or optionally substituted heterocycle; and $R_{11}$, $R_{12}$, and $R_{13}$ are each independently H, halo, optionally substituted alkyl, optionally substituted heteroalkyl optionally substituted aryl optionally substituted heteroaryl optionally substituted carbocycle, or optionally substituted heterocycle.

In some embodiments, $R_1$ is

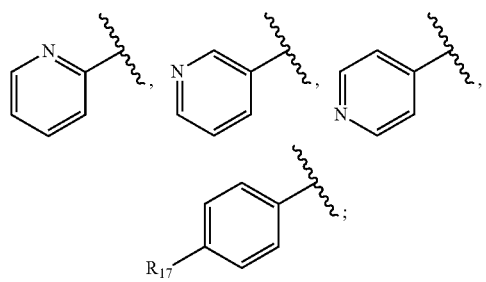

and $R_{17}$ is $C_1$-$C_6$ alkyl. In some embodiments, $R_1$ is

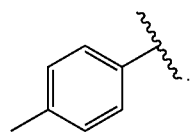

In some embodiments, $R_2$ is:

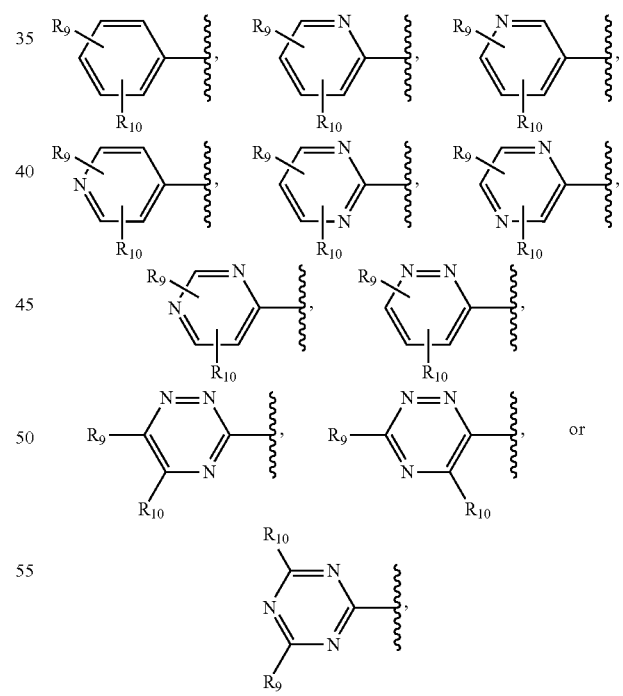

wherein $R_9$ and $R_{10}$ are each independently H, $OR_{14}$, $NR_{15}R_{16}$, $NO_2$, $SO_2NH_2$, halo, optionally substituted alkyl, optionally substituted heteroalkyl, optionally substituted aryl, optionally substituted heteroaryl, optionally substituted carbocycle, or optionally substituted heterocycle; and $R_{14}$, $R_{15}$, and $R_{16}$ are each independently H, halo, optionally .substituted alkyl, optionally substituted heteroalkyl, optionally substituted aryl, optionally substituted heteroaryl, optionally substituted carbocycle, or optionally substituted heterocycle.

In some embodiments, $R_2$ is:

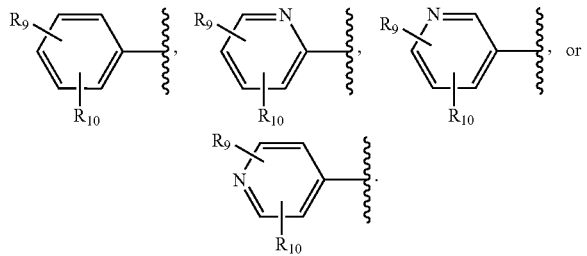

In some embodiments, $R_2$ is

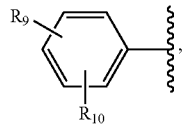

wherein $R_9$ and $R_{10}$ are independently H, halo, haloalkyl, $OR_{14}$, or $C_{1-6}$ alkyl. In some embodiments, $R_9$ and $R_{10}$ are independently H or $OR_{14}$. In some embodiments, $OR_{14}$ is alkoxy. In some embodiments, the alkoxy is methoxy, ethoxy, n-propoxy, isopropoxy, or t-butoxy. In some embodiments, $R_9$ is H and $R_{10}$ is $C_1$-$C_6$ alkyl. In some embodiments, prodrug thereof, wherein $R_9$ is H and $R_{10}$ is haloalkyl. In some embodiments, the haloalkyl is trifluoromethyl. In some embodiments, $R_9$ and $R_{10}$ are independently H or halo.

In some embodiments, $R_2$ is

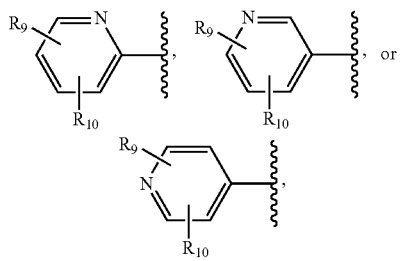

wherein $R_9$ and $R_{10}$ are independently H, halo, haloalkyl, $OR_{14}$, $NR_{15}R_{16}$ or $C_1$-$C_6$alkyl. In some embodiments, $R_2$ is

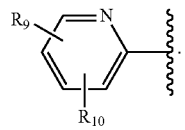

In some embodiments, $R_9$ and $R_{10}$ are independently H or $OR_{14}$. In some embodiments. $OR_{14}$ is alkoxy. In some embodiments, the alkoxy is methoxy, ethoxy, n-propoxy, isopropoxy, or t-butoxy. In some embodiments, $R_9$ and $R_{10}$ are independently H or $NR_{15}R_{16}$. In some embodiments, $R_9$ is H and $R_{10}$ is $NR_{15}R_{16}$. In some embodiments, $R_{15}$ and $R_{16}$ are independently $C_1$-$C_6$ alkyl. In some embodiments, $R_9$ and $R_{10}$ are independently H or $C_1$-$C_6$ alkyl. In some embodiments, $R_9$ is H and $R_{10}$ is $C_1$-$C_6$ alkyl. In some embodiments, $R_9$ and $R_{10}$ are independently H or halo. In some embodiments, $R_9$ is H and $R_{10}$ is halo. In some embodiments, $R_9$ and $R_{10}$ are H.

In some embodiments, $R_2$ is

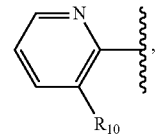

wherein $R_{10}$ is $C_1$-$C_6$ alkyl, —O—$R_{21}$—C(=O)$OR_{22}$, wherein, $R_{21}$ is $C_1$-$C_6$ alkyl and $R_{22}$ is $C_1$-$C_6$ alkyl or H. In some embodiments, wherein $R_{22}$ is $C_1$-$C_6$ alkyl. In some embodiments, $R_{22}$ is t-butyl. In some embodiments, $R_{10}$ is methyl or ethyl.

In some embodiments, $R_3$ is H, halo, —C(=O)$OR_{19}$,

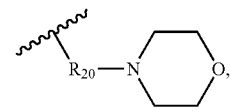

wherein $R_{19}$ is $C_1$-$C_6$ alkyl and $R_{20}$ is $C_1$-$C_6$ alkyl. In some embodiments, halo is bromo or chloro. In some embodiments. $R_{19}$ is methyl.

In some embodiments, the compound, or a pharmaceutically acceptable salt, ester or prodrug thereof, is selected from the group consisting of:

| Compound # | Structure |
|---|---|
| 1 | 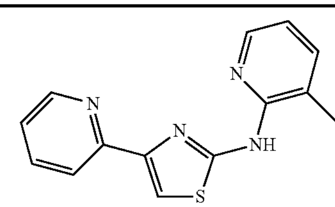 |
| 2 | 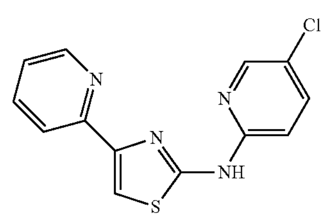 [SMILES: Clc1ccc(Nc2nc(-c3ccccn3)cs2)nc1] |
| 3 | 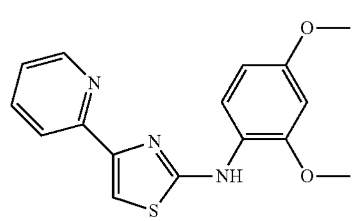 [SMILES: COc1ccc(Nc2nc(-c3ccccn3)cs2)c(OC)c1] |

-continued
| Compound # | Structure |
|---|---|
| 4 | 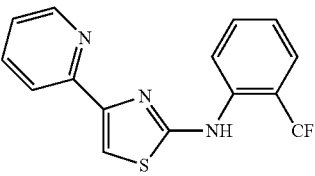 |
| 5 | 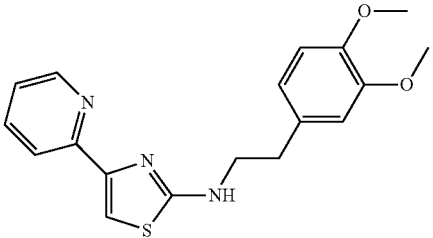 [SMILES: COc1ccc(CCNc2nc(-c3ccccn3)cs2)cc1OC] |
| 6 | 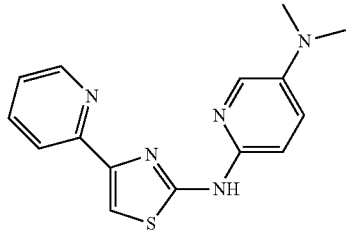 [SMILES: CN(C)c1ccc(Nc2nc(-c3ccccn3)cs2)nc1] |
| 7 | 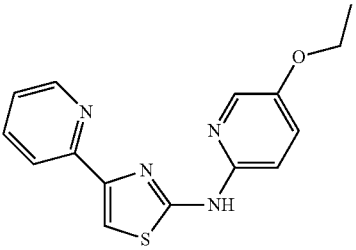 [SMILES: CCOc1ccc(Nc2nc(-c3ccccn3)cs2)nc1] |
| 8 | 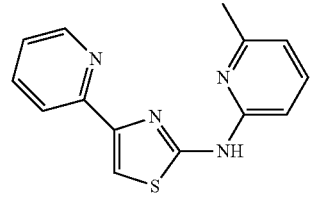 [SMILES: Cc1cccc(Nc2nc(-c3ccccn3)cs2)n1] |
| 9 | 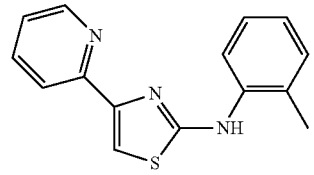 [SMILES: Cc1ccccc1Nc1nc(-c2ccccn2)cs1] |
| 10 | 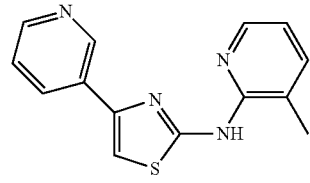 [SMILES: Cc1cccnc1Nc1nc(-c2cccnc2)cs1] |
-continued
| Compound # | Structure |
|---|---|
| 11 | 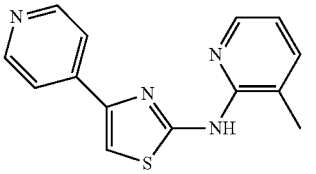 |
| 12 | 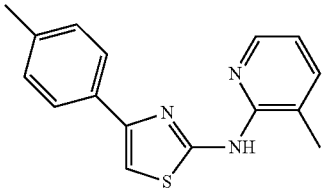 |
| 13 | 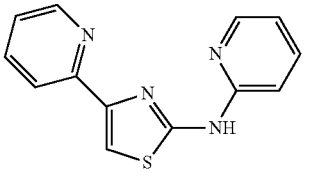 [SMILES: c1ccc(Nc2nc(-c3ccccn3)cs2)nc1] |
| 14 | 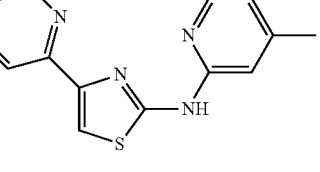 |
| 15 | 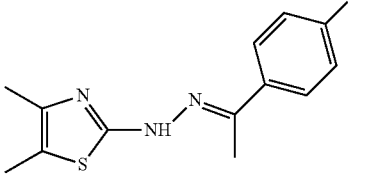 |
| 16 | 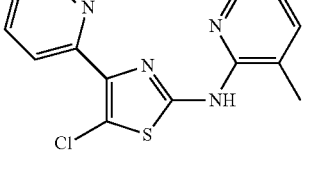 |
| 17 | 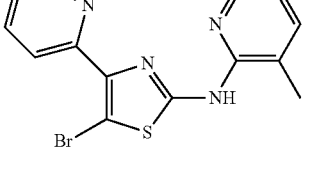 |
| 18 | 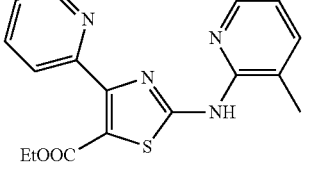 |

-continued
| Compound # | Structure |
|---|---|
| 19 | 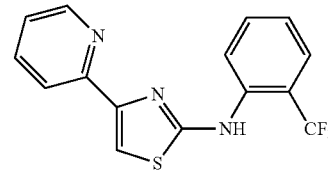 |
| 20 | 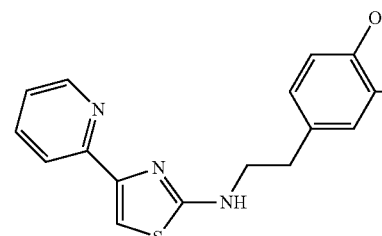 |
| 21 | 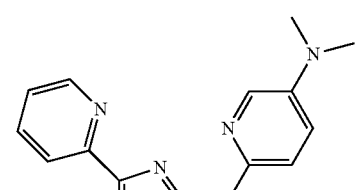 |
In some embodiments, a compound of Formula I, or a pharmaceutically acceptable salt, ester or prodrug thereof, is not one or more of a compound selected from the following table:
| Compound # | Structure |
|---|---|
| 1 | 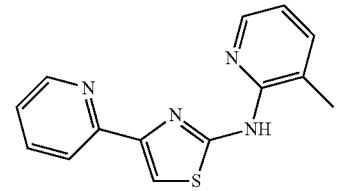 [SMILES: Cc1cccnc1Nc1nc(-c2ccccn2)cs1] |
| 2 | 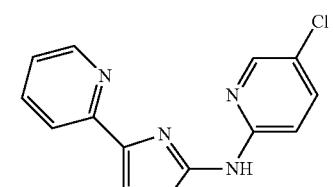 |
| 3 | 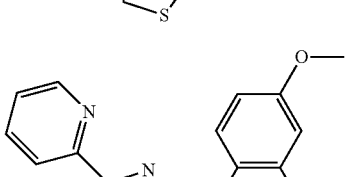 |
| 4 | 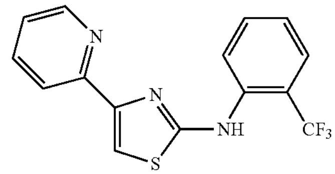 [SMILES: FC(F)(F)c1ccccc1Nc1nc(-c2ccccn2)cs1] |
| 5 | 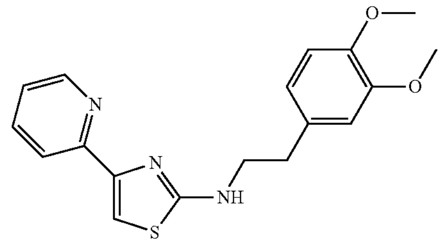 [SMILES: COc1ccc(CCNc2nc(-c3ccccn3)cs2)cc1OC] |
| 6 | 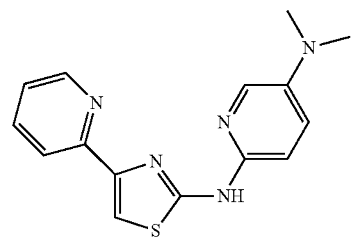 [SMILES: CN(C)c1ccc(Nc2nc(-c3ccccn3)cs2)nc1] |
| 7 | 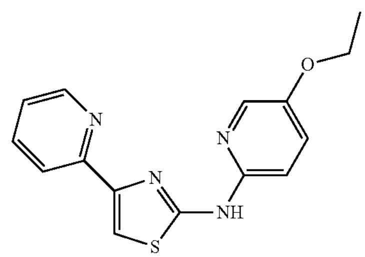 [SMILES: CCOc1ccc(Nc2nc(-c3ccccn3)cs2)nc1] |
| 8 | 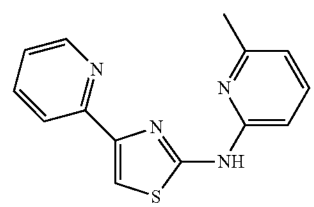 [SMILES: Cc1cccc(Nc2nc(-c3ccccn3)cs2)n1] |
| 9 | 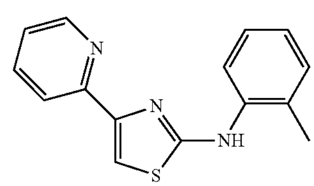 [SMILES: Cc1ccccc1Nc1nc(-c2ccccn2)cs1] |
| 10 | 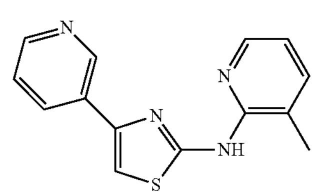 [SMILES: Cc1cccnc1Nc1nc(-c2cccnc2)cs1] |

-continued
| Compound # | Structure |
|---|---|
| 11 | 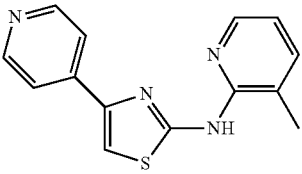 |
| 12 | 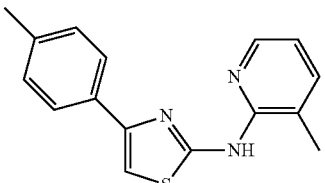 |
| 13 | 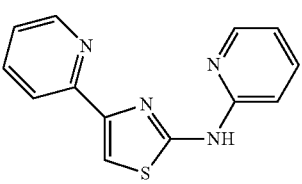 [SMILES: c1ccc(Nc2nc(-c3ccccn3)cs2)nc1] |
| 14 | 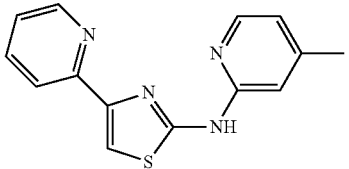 [SMILES: Cc1ccnc(Nc2nc(-c3ccccn3)cs2)c1] |
| 15 | 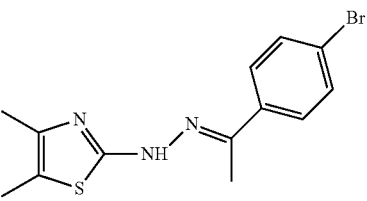 [SMILES: C/C(=N\Nc1nc(C)c(C)s1)c1ccc(Br)cc1] |
| 16 | 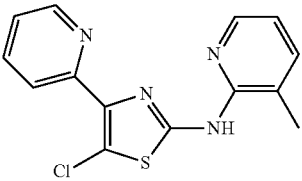 [SMILES: Cc1cccnc1Nc1nc(-c2ccccn2)c(Cl)s1] |
| 17 | 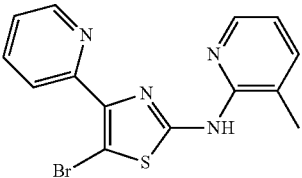 |
| 18 | 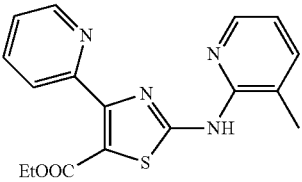 [SMILES: CCOC(=O)c1sc(Nc2ncccc2C)nc1-c1ccccn1] |
-continued
| Compound # | Structure |
|---|---|
| 19 | 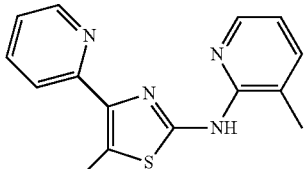 |
| 20 | 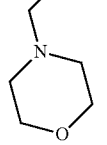 |
| 21 | 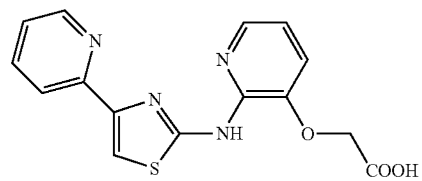 [SMILES: O=C(O)COc1cccnc1Nc1nc(-c2ccccn2)cs1] |
In some embodiments, the compound Formula I is not one or more of:
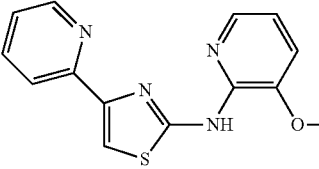
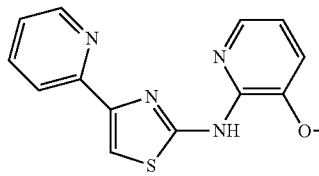
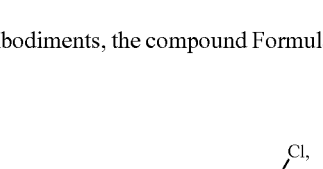

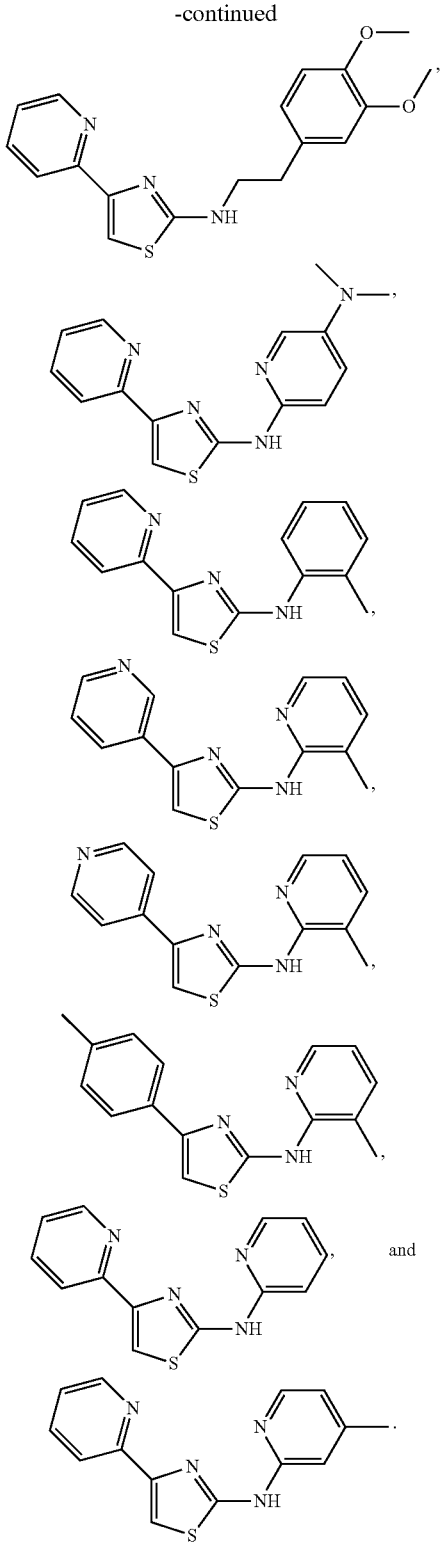

based upon the compounds desired and described herein. In some embodiments, the method is made according to the following schemes. In some embodiments, this method can be used to make one or more compounds as described herein and will be apparent to one of skill in the art which compounds can be made according to the methods described herein.

The following representative schemes illustrate how compounds described herein can be prepared. The specific solvents and reaction conditions referred to are also illustrative and are not intended to be limited. Compounds not described are either commercially available or are readily prepared by one skilled in the art using available starting materials.

The conditions and temperatures can be varied, such as shown in the examples described herein. These schemes are non-limiting synthetic schemes and the synthetic routes can be modified as would be apparent to one of skill in the art reading the present specification.

The compounds can be prepared according to any suitable method. Examples of the schemes that can be used to synthesize the compounds can be found in the Example sections. One of skill in the art would be able to modify these schemes to synthesize additional embodiments of the compounds, in some embodiments, one of the following scheme is used to prepare one or mote compounds:

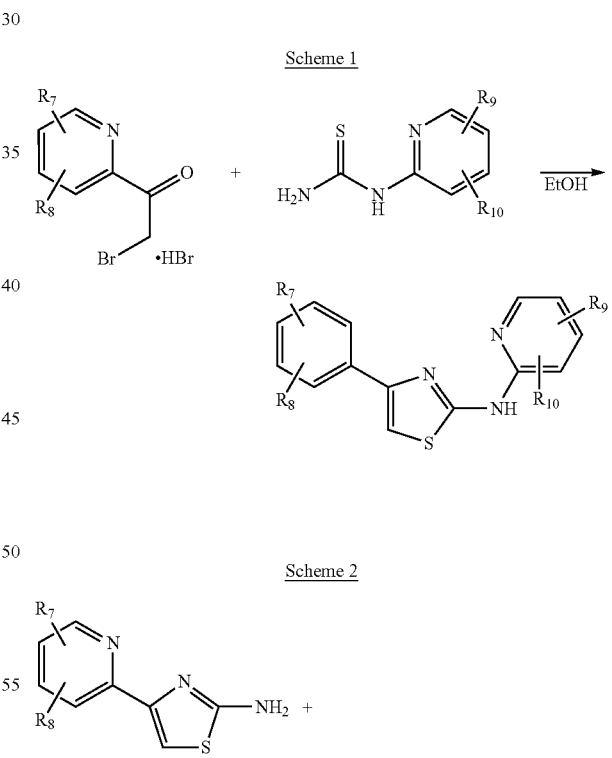

In some embodiments, the present invention provides pharmaceutical compositions comprising a compound, prodrug, or pharmaceutically salt thereof of any compound described herein.

The compounds described herein can be made by can be made according to the methods described herein and in the examples. The methods described herein can be adapted

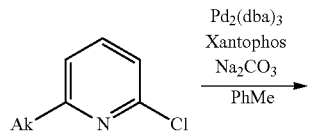

-continued

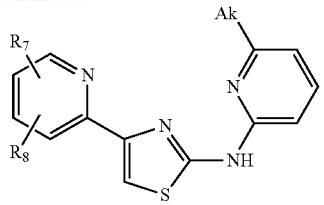

The substituents have the meanings provided for herein. The schemes can be modified in view of the examples and the knowledge of one of skill in the art to make the compounds of Formula I. Additionally, compounds having the dihydrobromide can also be made according to the methods and schemes provided herein.

In some embodiments, the compounds described herein can also be prepared according to the following scheme:

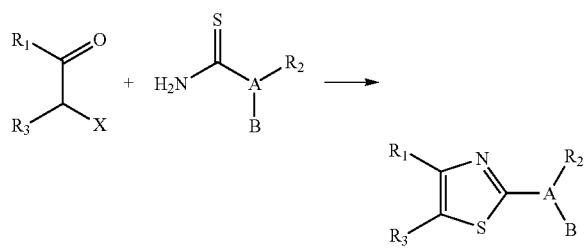

wherein:

$R_1$, $R_2$, $R_3$ are each independently, H, aryl, heteroaryl, alkyl arylalkyl heteroarylalkyl; optionally substituted carboxyl optionally substituted alkoxycarbonyl or optionally substituted aryloxycarbonyl X is a leaving group (e.g. a group considered as leaving group in the art of synthetic chemistry, such as, but not limited to, halo, OMs, OTs);

A is N or $(CH_2)q$; B: null, H, alkyl; and q is 1-6.

In some embodiments, the compounds described herein can also be prepared according to the following scheme:

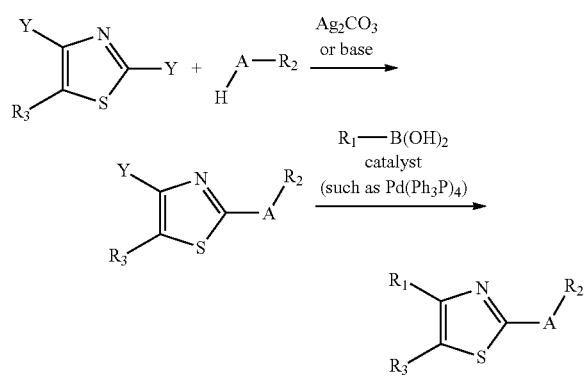

wherein:

$R_1$, $R_2$, $R_3$: independently, H, aryl, heteroaryl, alkyl, arylalkyl, heteroarylalkyl, optionally substituted carboxyl, optionally substituted alkoxycarbonyl, or optionally substituted aryloxycarbonyl;

X is a leaving group (e.g. a group considered as leaving group in the art of synthetic chemistry, such as, but not limited to, halo, GMs, OTs); and A: O or S. That catalyst shown in the scheme is a non-limiting catalyst and other catalysts can be used.

In some embodiments, the compounds described herein can also be prepared according to the following scheme:

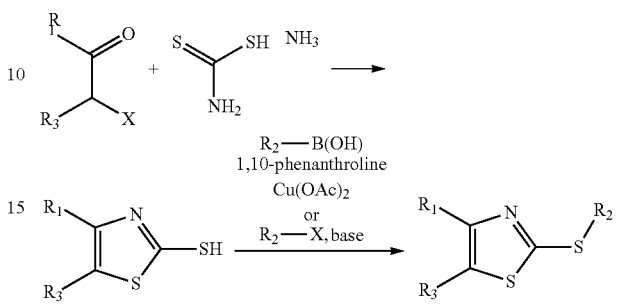

wherein:

$R_1$, $R_2$, $R_3$ are each independently, H, aryl, heteroaryl, alkyl, arylalkyl, heteroarylalkyl optionally substituted carboxyl, optionally substituted alkoxycarbonyl, or optionally substituted aryloxycarbonyl; and X is a leaving group (e.g. a group considered as leaving group in the art of synthetic chemistry, such as, but not limited to, halo, OMs, or OTs).

In some embodiments, the compounds described herein can also be prepared according to the following scheme:

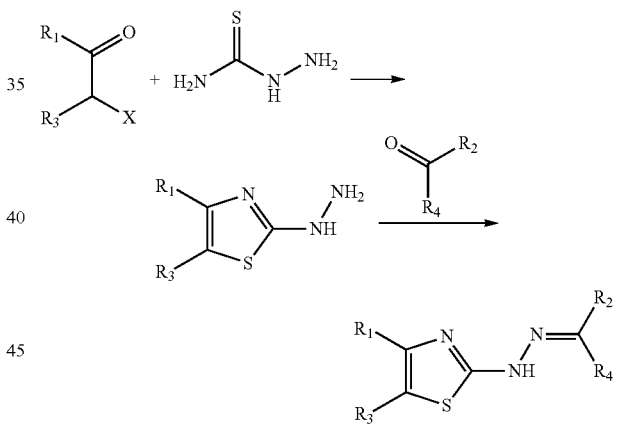

wherein;

$R_1$, $R_2$, $R_3$, $R_4$ are each independently, H, aryl, heteroaryl, alkyl, arylalkyl, heteroarylalkyl, optionally substituted carboxyl, optionally substituted alkoxycarbonyl or optionally substituted aryloxycarbonyl; and X is a leaving group (e.g. a group considered as leaving group in the art of synthetic chemistry, such as, but not limited to, halo, OMs, or OTs).

The compounds can also be prepared according to the embodiments described in the Examples. The examples and the schemes described herein can also be readily modified as necessary to yield other compounds described herein.

The compounds described herein can be administered in any conventional manner by any route where they are active. Administration can be systemic, topical, or oral. For example, administration can be, but is not limited to, parenteral, subcutaneous, intravenous, intramuscular, intraperitoneal, transdermal, oral, buccal, sublingual, or ocular routes, or intravaginally, by inhalation, by depot injections, or by implants. The mode of administration can depend on the conditions or disease to be targeted or treated. The selection of the specific route of administration can be selected or adjusted by the clinician according to methods known to the clinician to obtain the desired clinical response.

In some embodiments, it may be desirable to administer one or more compounds, or a pharmaceutically acceptable salt thereof, locally to an area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, wherein the implant is of a porous, non-porous, or gelatinous material, including membranes, such as sialastic membranes, or fibers.

The compounds described herein can be administered either alone or in combination (concurrently or serially) with other pharmaceuticals. For example, the compounds can be administered in combination with other analgesics, antidepressants, anti-anxiety compounds, anti-overactive bladder compounds, compounds for the treatment of Parkinsons, and the like. Examples of other pharmaceuticals or medicaments are known to one of skill in the art and include, but are not limited to those described herein.

The means and methods for administration are known in the art and an artisan can refer to various pharmacologic references for guidance (see, for example, Modern Pharmaceutics. Banker & Rhodes, Marcel Dekker, Inc. (1979); and Goodman & Gilman's The Pharmaceutical Basis of Therapeutics, 6th Edition, MacMillan Publishing Co., New York (1980)).

The amount of compound to be administered is that amount which is therapeutically effective. The dosage to be administered will depend on the characteristics of the subject being treated, e.g., the particular animal treated, age, weight, health, types of concurrent treatment, if any, and frequency of treatments, and can be easily determined by one of skill in the art (e.g., by the clinician). The standard dosing for protamine can be used and adjusted (i.e., increased or decreased) depending upon the factors described above. The selection of the specific dose regimen can be selected or adjusted or titrated try the clinician according to methods known to the clinician to obtain the desired clinical response.

The amount of a compound described herein that will be effective in the treatment and/or prevention of a particular disease, condition, or disorder will depend on the nature and extent of the disease, condition, or disorder, and can be determined by standard clinical techniques, in addition, in vitro or in vivo assays may optionally be employed to help identify optimal dosage ranges. The precise dose to be employed in the compositions will also depend on the route of administration, and the seriousness of the disorder, and should be decided according to the judgment of the practitioner and each patient's circumstances. However, a suitable dosage range for oral administration is, generally, from about 0.001 milligram to about 200 milligrams per kilogram body weight, from about 0.01 milligram to about 100 milligrams per kilogram body weight, from about 0.01 milligram to about 70 milligrams per kilogram body weight, from about 0.1 milligram to about 50 milligrams per kilogram body weight, from 0.5 milligram to about 20 milligrams per kilogram body weight, or from about 1 milligram to about 10 milligrams per kilogram body weight. In some embodiments, the oral dose is about 5 milligrams per kilogram body weight.

In some embodiments, suitable dosage ranges for intravenous (i.v.) administration are from about 0.01 mg to about 500 mg per kg body weight, from about 0.1 mg to about 100 mg per kg body weight, from about 1 mg to about 50 mg per kg body weight, or from about 10 mg to about 35 mg per kg body weight. Suitable dosage ranges for other modes of administration can be calculated based on the forgoing dosages as known by those skilled in the art. For example, recommended dosages for intranasal, transmucosal, intradermal, intramuscular, intraperitoneal, subcutaneous, epidural, sublingual, intracerebral, intravaginal, transdermal administration or administration by inhalation are in the range of from about 0.001 mg to about 200 mg per kg of body weight, from about 0.01 mg to about 100 mg per kg of body weight, from about 0.1 mg to about 50 mg per kg of body weight, or from about 1 mg to about 20 mg per kg of body weight. Effective doses may be extrapolated from dose-response curves derived from in vitro or animal model test systems. Such animal models and systems are well known in the art.

The compounds described herein can be formulated for parenteral administration by injection, such as by bolus injection or continuous infusion. The compounds can be administered by continuous infusion subcutaneously over a period of about 15 minutes to about 24 hours. Formulations for injection can be presented in unit dosage form, such as in ampoules or in multi-dose containers, with an optionally added preservative. The compositions can take such forms as suspensions, solutions or emulsions in oily or aqueous vehicles, and can contain formulatory agents such as suspending, stabilizing and/or dispersing agents. In some embodiments, the injectable is in the form of short-acting, depot, or implant and pellet forms injected subcutaneously or intramuscularly. In some embodiments, the parenteral dosage form is the form of a solution, suspension, emulsion, or dry powder.

For oral administration, the compounds described herein can be formulated by combining the compounds with pharmaceutically acceptable carriers well known in the art. Such carriers enable the compounds to be formulated as tablets, pills, dragees, capsules, emulsions, liquids, gels, syrups, caches, pellets, powders, granules, slurries, lozenges, aqueous or oily suspensions, and the like, for oral ingestion by a patient to be treated. Pharmaceutical preparations for oral use can be obtained by, for example, adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethylcellulose, sodium carboxymethylcellulose, and polyvinylpyrrolidone (PVT). If desired, disintegrating agents cat) be added, such as, but not limited to, the cross-linked polyvinyl pyrrolidone, agar, or alginic acid or a sail thereof such as sodium alginate.

Orally administered compositions can contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds. Oral compositions can include standard vehicles such as mannitol, lactose, starch, magnesium stearate, sodium saccharine, cellulose, magnesium carbonate, etc. Such vehicles are suitably of pharmaceutical grade.

Dragee cores can be provided with suitable coatings. For this purpose, concentrated sugar solutions can be used, which can optionally contain gum arable, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include, but are not limited to, push-fit capsules made of gelatin, as well as soft, sealed capsules made of gelatin and a plasticizer, such as glycerol or sorbitol The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added.

For buccal administration, the compositions can take the form of, such as, tablets or lozenges formulated in a conventional manner.

For administration by inhalation, the compounds described herein can be delivered in the form of an aerosol spray presentation from pressurized packs or a nebulizer, with the use of a suitable propellant, such as dychlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, such as gelatin for use in an inhaler or insufflator can be formulated containing a powder mix of the compound and a suitable powder base such as lactose or starch.

The compounds described herein can also be formulated in rectal compositions such as suppositories or retention enemas, such as containing conventional suppository bases such as cocoa butter or other glycerides. The compounds described herein can also be formulated in vaginal compositions such as vaginal creams, suppositories, pessaries, vaginal rings, and intrauterine devices.

In transdermal administration, the compounds can be applied to a plaster, or can be applied by transdermal, therapeutic systems that are consequently supplied to the organism. In some embodiments, the compounds are present in creams, solutions, powders, fluid emulsions, fluid suspensions, semi-solids, ointments, pastes, gels, jellies, and foams, or in patches containing any of the same.

The compounds described herein can also be formulated as a depot preparation. Such long acting formulations can be administered by implantation (for example subeutaneously or intramuscularly) or by intramuscular injection. Depot injections can be administered at about 1 to about 6 months or longer intervals. Thus, for example, the compounds can be formulated with suitable polymeric or hydrophobic materials (for example as an emulsion in an acceptable oil ) or ion exchange resins, or as sparingly soluble derivatives, for example, as a sparingly soluble salt.

In some embodiments, the compounds can be delivered in a controlled release system. In one embodiment, a pump may be used (see linger, supra; Sefton, CRC Crit. Ref. Biomed. Eng., 1987, 14, 201; Buchwald et al., Surgery, 1980, 88,507 Saudek et al., N. Engl. J. Med, 1989, 321, 574). In some embodiments, polymeric materials can be used (see Medical Applications of Controlled Release, Langer and Wise (eds.), CRC Pres., Boca Raton, Fla. (1974); Controlled Drug Bioavailability. Drug Product Design and Performance, Smolen and Ball (eds.), Wiley, New York (1984); Ranger et al., J. Macromol. Sci. Rev. Macromol. Chem., 1983, 23 ,61; see, also Levy et al., Science, 1985, 228, 190; During et al., Ann. Neurol. 1989, 25, 351; Howard et al., J. Neurosurg., 1989, 71, 105 ). In yet another embodiment, a controlled-release system can be placed in proximity of the target of the compounds described herein, such as the liver, thus requiring only a fraction of the systemic dose (see, e.g., Goodson, in Medical Applications of Controlled Release, supra., vol. 2, pp. 115-138 (1984)). Other controlled-release systems discussed in the review by Langer, Science, 1990, 249, 1527-1533) may be used.

It is also known in the art that the compounds can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The pharmaceutical compositions can also comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols. In some embodiments, the compounds described herein can be used with agents including, but not limited to, topical analgesics (e.g., lidocaine), barrier devices (e.g., GelClair), or rinses (e.g., Caphosol).

In some embodiments, the compounds described herein can be delivered in a vesicle, in particular a liposome (see, Langer, Science, 1990, 249, 1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

Suitable compositions include, but are not limited to, oral non-absorbed compositions. Suitable compositions also include, but are not limited to saline, water, cydodextrin solutions, and buffered solutions of pH 3-9.

The compounds described herein, or pharmaceutically acceptable salts thereof, can be formulated with numerous excipients including, but not limited to, purified water, propylene glycol, PEG 400, glycerin, DMA, ethanol, benzyl alcohol, citric acid/sodium citrate (pH3), citric acid/sodium citrate (pH5), tris(hydroxymethyl)amino methane HCl (pH7.0), 0.9% saline, and 1.2% saline, and any combination thereof. In some embodiments, excipient is chosen from propylene glycol, purified water, and glycerin.

In some embodiments, the formulation can be lyophilized to a solid and reconstituted with, for example, water prior to use.

When administered to a mammal (e.g., to an animal for veterinary use or to a human for clinical use) the compounds can be administered in isolated form.

When administered to a human, the compounds can be sterile. Water is a suitable carrier when the compound of Formula I is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The compositions described herein can take the form of a solution, suspension, emulsion, tablet, pill, pellet, capsule, capsule containing a liquid, powder, sustained-release formulation, suppository, aerosol, spray, or any other form suitable for use. Examples of suitable pharmaceutical carriers are described in Remington's Pharmaceutical Sciences, A. R. Gennaro (Editor) Mack Publishing Co.

In some embodiments, the compounds are formulated in accordance with routine procedures as a pharmaceutical composition adapted for administration to humans. Typically, compounds are solutions in sterile isotonic aqueous buffer. Where necessary, the compositions can also include a solubilizing agent. Compositions for intravenous administration may optionally include a local anesthetic such as lidocaine to case pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the compound is to be administered by infusion, it can be dispensed, for example, with an infusion bottle containing sterile pharmaceutical grade water or saline. Where the compound is administered by injection, an ampoule of sterile water for injection or saline can be provided so that the ingredients may be mixed prior to administration.

The pharmaceutical compositions can be in unit dosage form. In such form, the composition can be divided into unit doses containing appropriate quantities of the active component. The unit dosage form can be a packaged preparation, the package containing discrete quantities of the preparations, for example, packeted tablets, capsules, and powders in vials or ampules. The unit dosage form can also be a capsule, cachet, or tablet itself, or it can be the appropriate number of any of these packaged forms.

In some embodiments, a composition of the present invention is in the form of a liquid wherein the active agent (i.e., one of the facially amphiphilic polymers or oligomers disclosed herein) is present in solution, in suspension, as an emulsion, or as a solution/suspension. In some embodiments, the liquid composition is in the form of a gel. In other embodiments, the liquid composition is aqueous. In other embodiments, the composition is in the form of an ointment.

In some embodiments, the composition is in the form of a solid article. For example, in some embodiments, the ophthalmic composition is a solid article that can be inserted in a suitable location in the eye, such as between the eye and eyelid or in the conjunctival sac, where it releases the active agent as described, for example, U.S. Pat. Nos. 3,863,633; 3,867,519; 3,868,445; 3,960.150; 3,963,025; 4,186,184: 4,303,637: 5,443,505; and 5,869,079. . Release from such an article is usually to the cornea, either via the lacrimal fluid that bathes the surface of the cornea, or directly to the cornea itself with which the solid article is generally in intimate contact. Solid articles suitable for implantation in the eye in such fashion are generally composed primarily of polymers and can be bioerodible or non-bioerodible. Bioerodible polymers that can be used in the preparation of ocular implants carrying one or more of the anti-microbial, facially amphiphilic polymer or oligomer active agents in accordance with the present invention include, but are not limited to, aliphatic polyesters such as polymers and copolymers of poly(glycolide), poly(lactide), poly(epsilon-caprolactone), poly-(hydroxybutyrate) and poly(hydroxyvalerate), polyamino acids, polyorthoesters, polyanhydrides, aliphatic polycarbonates and polyether lactones. Suitable non-bioerodible polymers include silicone elastomers.

The compositions described herein can contain preservatives. Suitable preservatives include, but are not limited to, mercury-containing substances such as phenylmercuric salts (e.g., phenylmercuric acetate, borate and nitrate) and thimeroxal: stabilized chlorine dioxide; quaternary ammonium compounds such as benzalkonium chloride, cetyltrimethylammonium bromide and cetylpyridinium chloride; imidazolidinyl urea; parabens such as methylparaben, ethylparaben, propylparaben and butylparaben, and salts thereof; phenoxyethanol; chlorophenoxyethanol; phenoxypropanol; chlorobutanol; chlorocresol; phenylethyl alcohol; disodium EDTA; and sorbic acid and salts thereof.

Optionally one or more stabilizers can be included in the compositions to enhance chemical stability where required. Suitable stabilizers include, but are not limited to, chelating agents or complexing agents, such as, for example, the calcium complexing agent ethylene diamine tetraacetic acid (EDTA), For example, an appropriate amount of EDTA or a salt thereof, e.g., the disodium salt, can be included in the composition to complex excess calcium ions and prevent gel formation during storage. EDTA or a salt thereof can suitably be included in an amount of about 0.01% to about 0.5%. in those embodiments containing a preservative other than EDTA, the EDTA or a salt thereof more particularly disodium EDTA, can be present in an amount of about 0.025% to about 0.1% by weight.

One or more antioxidants can also be included in the compositions. Suitable antioxidants include, but are not limited to, ascorbic acid, sodium metabisulfite, sodium bisulfite, acetylcysteine, polyquaternium-1, benzalkonium chloride, thimerosal, chlorobutanol, methyl paraben, propyl paraben, phenylethyl alcohol, edetate disodium, sorbic acid, or other agents know to those of skill in the art. Such preservatives are typically employed at a level of from about 0.001% to about 1.0% by weight.

One or more acceptable pH adjusting agents and/or buffering agents can be included in the compositions, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in art acceptable range.

One or more acceptable salts can be included in the compositions of the invention in an amount required to bring osmolality of the composition into an acceptable range. Such salts include, but are not limited to, those having sodium, potassium or ammonium cations and chloride, citrate, ascorbate, borate, phosphate, bicarbonate, sulfate, thiosulfate or bisulfite anions. In some embodiments, salts include sodium chloride, potassium chloride, sodium thiosulfate, sodium bisulfite and ammonium sulfate. In some embodiments, the salt is sodium chloride.

Optionally one or more acceptable surfactants, preferably nonionic surfactants, or co-solvents can be included in the compositions to enhance solubility of the components of the compositions or to impart physical stability, or for other purposes. Suitable nonionic surfactants include, but are not limited to, pulyoxyethylene fatty acid glycerides and vegetable oils, e.g., polvoxycthylene (60) hydrogenated castor oil; and polyoxyethylene alkylethers and alkylphenyl ethers, e.g., octoxynol 10, octoxynol 40; polysorbate 20, 60 and 80; polyoxyethylene/polyoxypropylene surfactants (e.g., Pluronic® F-68, F84 and P-103); cyclodextrin; or other agents known to those of skill in the art. Typically, such co-solvents or surfactants are employed in the compositions at a level of from about 0.01% to about 2% by weight.

The present invention also provides pharmaceutical packs or kits comprising one or more containers tilled with one or more compounds described herein. Optionally associated with such container(s) can be a notice in the form prescribed by a governmental agency regulating the manufacture, use or sale of pharmaceuticals or biological products, which notice reflects approval by the agency of manufacture, use or sale for human administration for treating a condition, disease, or disorder described herein. In some embodiments, the kit contains more than one compound described herein. In some embodiments, the kit comprises a compound described herein in a single injectable dosage form, such as a single dose within an injectable device such as a syringe with a needle.

The present invention also provides methods of treating tuberculosis. In some embodiments, the method comprises administering to a subject with tuberculosis or suspected of having tuberculosis a compound, or a pharmaceutically acceptable salt, ester or prodrug thereof, or pharmaceutical composition described herein. In some embodiments, the compounds are for the treatment of tuberculosis in a subject in need thereof. The treatment of tuberculosis can be targeted against replicating or non-replicating tuberculosis, in some embodiments, the compounds selectively target either replicating or non-replicating tuberculosis. Selective targeting of one form of tuberculosis over another means that the compound, or a pharmaceutically acceptable salt, ester or prodrug thereof, has at least a 2, 3, 4, 5, 6, 7, 8, 9, 10 fold preference for one form or other. Preference can be determined by comparing the $IC_{90}$ of the compound against replicating tuberculosis and the $IC_{99}$ of the compound against non-replicating tuberculosis. For example, if the compound has a 10 μm $IC_{99}$ against non-replicating tuberculosis and a 10 μm $IC_{90}$ against, replicating tuberculosis the compound is said to have a 10 fold preference for non-replicating tuberculosis. The $IC_{90}$ of the compound against replicating tuberculosis and the $IC_{99}$ of the compound against non-replicating tuberculosis can be determined by any method.

For example, but not limited to, to determine the $IC_{99}$ of the compound against non-replicating tuberculosis a non-replicating, carbon-starvation assay can be used. Carbon starvation conditions can be used as a means of nutrient depriving bacilli in order to induce a non-replicating, drug tolerant stale. The bacilli can be starved for 6 weeks in phosphate-buffered saline (PBS), resulting in bacteria that were refractory to standard antibiotics at doses up to 10 times the minimum inhibitory concentration (MIC). This assay is then adapted to a high throughput screen (HTS) against carbon starved TB in appropriate growth medium. An example of growth medium is, but not limited to, 7H9/tyloxapol (0.05%), which includes several cofactors (biotin, pyridoxine, iron), trace metals, and some nitrogen source (ammonium sulfate). This buffer can be used to replicate carbon starvation while still providing some minimal essential nutrients. Under these conditions are instituted, no killing will be observed with control anti-tuberculosis antibiotics, such as rifampin and isoniazid at 10× MIC (MIC: rifampin 0.01 ug/mL and INH 0.1 ug/mL). The TB can be a TB strain that has been modified to express a fluorescent protein, such as GFP. An example of such a strain is *M. tuberculosis* H37Rv strain, which expresses constitutive, episomal GFP. Fluorescence can then be used to measure cell survival. The bacteria can also be transitioned back to replicating state by the addition of 5× rich media, followed by a 4 day period of outgrowth of replicating cells. Other examples of the assay are described in the examples section herein.

The present invention also provides one or more compounds described above, or a pharmaceutically acceptable salt thereof, or a pharmaceutical composition comprising one or more compounds described above, for use in the manufacture of a medicament for the treatment of tuberculosis. Any other known medicament, compound, or composition use for the treatment of tuberculosis can be used in co-therapy, co-administration or co-formulation with a composition or compound as described herein.

Frequency of administration is typically such that the dosing interval, for example, the period of time between one dose and the next, during waking hours is from about 2 to about 12 hours, from about 3 to about 8 hours, or from about 4 to about 6 hours. It will be understood by those of skill in the art that an appropriate dosing interval is dependent to some degree on the length of time for which the selected composition is capable of maintaining a concentration of the compound(s) in the subject and/or in the target tissue (e.g., above the $EC_{50}$ (the minimum concentration of the compound which modulates the receptor's activity by 90%). Ideally the concentration remains above the $EC_{50}$ for at least 100% of the dosing interval. Where this is not achievable it is desired that the concentration should remain above the $EC_{50}$ for at least about 60% of the dosing interval, or should remain above the $EC_{50}$ for at least about 40% of the dosing interval.

In order that the embodiments disclosed herein may be more efficiently understood, examples are provided below, it should be understood that these examples are for illustrative purposes only and are not to be construed as limiting in any manner.

EXAMPLES

Assays used to measure growth or inhibition of TB.

Bacterial strains and growth conditions. The strain *M. tuberculosis* H37Rv was used for all experiments. OFF was expressed using a constitutive episomal plasmid driven by the Rv3583c promoter. An inducible firefly luciferase expression plasmid was constructed using an anhydroietracyeltne inducible system, as described previously (30). Mtb H37Rv was grown at 37° C. in Middlebrook 7H9 broth supplemented with 10% OADC (oleic acid-albumin-dextrose complex), 0.2% glycerol and 0.05% Tween-80 or on Middlebrook 7H10 plates supplemented with 10% OADC enrichment.

Carbon Starvation. Freezer stocks of H37Rv were diluted 1:50 in fresh 7H9 OADC media and cultured until late log phase. $OD_{600}$ between 0.6 and 1.0. The bacteria were centrifuged at 2800× g for five minutes and resuspended in 50 mL of starvation media (7H9 and 0.05% Tyloxapol without any supplementation). The cells were then washed an additional two times with starvation media. After the final wash the cells were resuspended in starvation media to an $OD_{600}$ of 0.2 and 50 ml of culture aliquoted into a sterile roller bottle. The starvation culture was incubated standing at 37° C. for 5 weeks.

Compound Testing: An initial assay was developed and utilized using a GFP-expressing *M. tuberculosis* reporter strain that measured fluorescence as a marker for growth and survival after an outgrowth period in rich 7H9 media. This assay was modified to accommodate the scale of the screen involving the MLPCN library. These modifications include using Alamar blue to measure surviving bacteria rather than the fluorescence, and outgrowth in 7H12 media.

Carbon starvation assays. For *M. tuberculosis* starvation screening assays, carbon-starved bacteria expressing GFP were diluted and plated into 384 well plates into which compounds had previously been pinned for a final OD600 of 0.05, a final volumes of 40 µL and a final compound concentration of 30 µM. Plates were incubated for a period of 120 h. at which time 10 µL 5× concentrated media was added to each well of the plate (7H9 media with 50% OADC, 1% glyceroln 0.05 % tyloxapol). Plates were then incubated for an additional 96 hours, at which time fluorescence was read using an M5 Spectramax. Each compound was screened in duplicate, and composite z-scores were calculated using DMSO controls as reference. Compounds were compounds that could inhibit growth or kill *M. tuberculosis* were defined as compounds with a composite z-score of less than −6. This z-score cutoff was selected as the z score of the concentration of the control antibiotic rifampicin that gave a Z'-factor of 0.

Alternative Carbon starvation assay. Carbon starved bacteria were diluted and plated into 384 well plates into which compounds had already been pinned for a final OD600 of 0.005 and final volume of 50 uL. The plates were incubated for 96 hours, at which time 12 uL of concentrated media was added. Plates were incubated for an additional 72 hours. For Alamar blue detection, a solution of 3 parts 18.2% Tween-80 to 4 parts Alamar Blue (3/7th Tween-80 to 4/7th Alamar Blue) is made and 9 ul added to each well in the plate. The plates are incubated (stacked 2-3 high) overnight at 37° C. in humidified incubator. The plates are removed from the incubator and sealed with aluminum seals. The fluorescence is read using the Envision plate reader (bottom read) with an excitation wavelength of 531 nm and an emission wavelength of 595 nm (Excitation filter=BODIPY TMR FP 531, barcode 105; Emission filter=Photometric 595, barcode 315; Mirror=BODIPY TMR, barcode 405).

Replicating, logarithmic assay. For *M. tuberculosis* screening assays for logarithmically growing, actively replicating activity, bacteria expressing GFP was grown to mid-log phase (OD600=0.6–0.8), diluted, and plated into 384 well plates into which compounds had previously been pinned for a final OD600 of 0.025. Elates were incubated for a period of 72 h, at which time GFP fluorescence is read. Each compound is screened in duplicate, and composite z-scores were calculated using DMSO controls as reference. Compounds that inhibit replicating *M. tuberculosis* were defined as compounds with a composite z-score of less than −4. This z-score cutoff was selected using average of the z-scores of the concentrations of the control antibiotics clofazimine and rifampicin that gave a Z'-factor of 0.

Replicating IC99 determination by OD600. For dose response curves and IC90 determinations by OD600, bacteria w ere grown to mid-log phase and plated in 96 well plates at OD6O0=0.05 in the presence of small molecule inhibitors for 7 days unless otherwise indicated, and growth was assessed by reading OD600. The IC90 was defined as the minimum concentration that inhibited growth by 90% relative to the DMSO control (31).

Non-replicating IC99 determination by luciferase. For the luciferase assay it test for activity of small molecules directly on non-replicating cells without an outgrowth phase, carbon-starved *M. tuberculosis* H37Rv containing an inducible firefly luciferase plasmid was dispersed into 96-well plates containing the small molecules and anhydotetracydine 50 nM (to induce luciferase expression). After 5 days the cells were lysed, luciferase reagent added and luminescence measured (Promega Corporation, Madison Wis.) in a Spcctramax M5 (Molecular Devices). The antibiotic rifampicin (at 80X the MIC) was used as a positive control for the assay.

Replicating IC90 determinations by CFU. To confirm the replicating IC90 values determined using OD600, the activity of selected small molecules were tested by plating fur colony forming units (CFU). *M. tuberculosis* H3Rv was grown to mid-log phase and plated in 96 well plates at OD600=0.025 in the presence of small molecule inhibitors for specified time periods. The number of surviving bacteria was then determined by plating a dilution series of the culture for colony forming units (CFU). The IC90 was defined the concentration tested that inhibited growth by at least 90% relative to the DMSO control.

Non-replicating IC90 determinations by CFU. To confirm the non-replicating IC90 values determined using the luciferase reporter, the activity of selected small molecules was tested by plating for CFU. Carbon-starved bacteria were diluted to OD600=0.05 in starvation media and plated in 96 well plates, in the presence of small molecule inhibitors for indicated time periods. The number of surviving bacteria was then determined by plating a dilution series of the culture for colony forming units (CFU). The IC90 was defined as the concentration tested that inhibited survival by at least 90% relative to the DMSO control.

Generating resistant mutants. The MIC of each compound on solid media was identified by plating $10^7$ bacteria on agar containing a dose response in 96 well plate format. The MIC was defined as the lowest concentration resulting in inhibition of bacterial growth. Resistant mutants were generated by plating *M. tuberculosis* cells onto agar pads containing 2× and 10× the agar MIC of each compound using four independently derived wild-type clones. Colonies that arose on inhibitor containing plates were inoculated into liquid media containing 1× the liquid MIC of the inhibitor. These cultures were grown to mid-log and samples were retested in a liquid MIC assay to confirm that a shift relative to the wild-type MIC was observed.

Macrophage toxicity assay. To determine macrophage toxicity, J774 macrophages were plated in 96 well plates at a concentration of $6.25 \times 10^4$ cells/well and rested overnight. A dilution series of the small molecule being tested was then added to the plates in quadruplicate. The top concentration tested was 50 uM. The plates were incubated for 48 hours, upon which time CellTiter-Glo (Promega Corporation) was used as a readout for macrophage viability.

Example 2

Synthesis of Compounds

Reagents and solvents were obtained from commercial suppliers and were used without further purification. Analytical LCMS was conducted on an Agilent Poroshell 120 EC-C18 column (30 mm×3.0 mm i.d.), eluting with 0.01% formic acid in water (solvent A) and 0.01% in acetonitrile (solvent B), using the following elution gradient: 0.00 min-0.03 min (5% B), 0.03 min-1.78 min (5% to 95% B, linear gradient), 1.78-2.28 min (95% B). 2.28-2.30 min (95% to 5% B, linear gradient), 2.30-2.50 min (5% B) at a flow rate of 1.75 ml/min and the mass spectra were recorded in elcctrospray positive and/or negative ion modes (ESI+and ESI−) on a Waters ZQ mass spectrometer. Preparative HPLC was performed on Varian ProStar system on a Agilent ZORBAX XDB-C18 column (150 mm×21/2 mm i.d.), eluting with water (solvent A) and acetonitrile (solvent B), using the following elution gradient: 0 in (50% B), 5 min (50% B), 14 min (95% B), 17 min (95% B) at a flow rate of 20 ml/min. $^1$H NMR spectra (300 MHz or 400 MHz) and $^{13}$C-NMR (75 MHz) were recorded on a Bruker spectrometer and chemical shifts are reported in parts per million (ppm, δ) downfield from tetramethylsilane (TMS). Coupling constants (J) are reported in Hz. Spin multiplicities are described as s (singlet), brs (broad singlet), t (triplet), q (quartet), and m (multiplet). Microwave reactions were performed in a Biotage Initiator 60 EXP microwave reactor.

Synthesis of N-(3-methylpyridin-2-yl)-4-(pyridin-2-yl) thiazol-2-amine (1). The compound was prepared according to the following scheme:

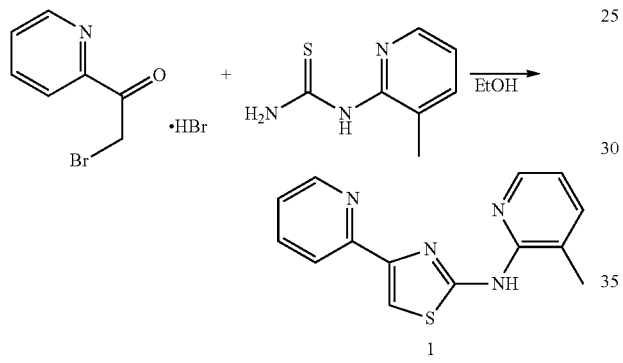

Specifically, a mixture of 2-(2-bromoacetyl)pyridine hydrobromide (421 mg, 1.50 mmol) and 1-(3-methyl-2-pyridyl) thiourea (251 mg, 1.50 mmol) in ethanol (15 ml) was stirred at 80° C. for 5 h. After cooled to room temperature the mixture was evaporated and the residue was partitioned between AcOEt and 10% aqueous K$_2$CO$_3$. Organic phase was washed with brine, dried over Na$_2$SO$_4$ and evaporated. The residue was crystallized from ethanol to give compound I (325 mg, 81% yield). $^1$H NMR (300 MHz, DMSO-d$_6$) δ 10.52 (s. 1H), 8.63-8.56 (m, 1H), 8.19 (dd, J=4.8, 1.2 Hz, 1H), 8.05 (d, J=7.9 Hz, 1H), 7.87 (td, J=7.7, 1.8 Hz, 1H), 7.66 (s, 1H), 7.57 (dd, J=7.2, 0.6 Hz, 1H), 7.31 (ddd, J=7.5, 4.8, 1.1 Hz, 1H), 6.92 (dd, J=7.3, 5.0 Hz, 1H), 2.37(s, 3H). 13C NMR (75 MHz, DMSO-d$_6$)δ 160.10, 152.56, 150.00, 149.37, 148.83, 143.29, 138.54, 137.05, 122.44, 119.93, 119.30, 116.37, 109.91, 16.85.

Synthesis of N-(6-methylpyridin-2-yl)4-(pyridin-2-yl)thiazol-2-amine (7). The compound was prepared according to the following scheme:

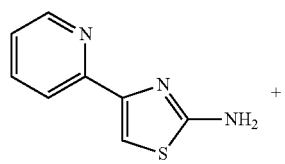

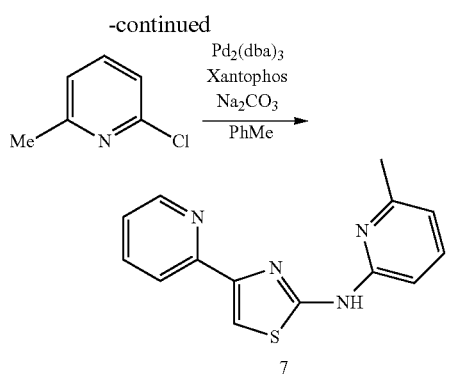

Specifically, a mixture of 4-(pyridine-2-yl)thiazole-2-amine (53 mg, 0.30 mmol), 2-chloro-6-methylpyridine (27.7 ul. 0.25 mmol), powdered Na$_2$CO$_3$ (39 mg, 0.37 mmol), Xantphos (25 mg, 0.04 mmol) and Pd$_2$ (dba)$_3$(20 mg. 0.02 mmol) in toluene (1 ml) was heated at 150° C. for 30 min under microwave irradiation. After cooled to room temperature the mixture was diluted with AcOEt and filtered to remove insoluble. The filtrate was evaporated. The residue was purified by preparative reversed phase HPLC (C18, 50–95% acetonitrile in water) to give compound 7(17 mg, 25% yield). $^1$H NMR (300 MHz, DMSO-d$_6$) δ 11.39 (s, 1H), 8.62-8.53 (m, 1H), 7.96 (dd. J=7.7, 0.8, 1H), 7.87 (td, J=7.9, 1.8, 1H), 7.65 (s, 1H), 7.60 (t, J=7.8. 1H), 7.35-7.25 (m, 1H), 6.89 (d, J=8.2, 1H), 6.80 (d, J=7.3, 1H), 2.47 (s, 3H).

Synthesis of 4-(pyridin-2-yl)-N-(o-tolyl)thiazol-2-amine dihydrohormide (8). The compound was prepared according to the following scheme:

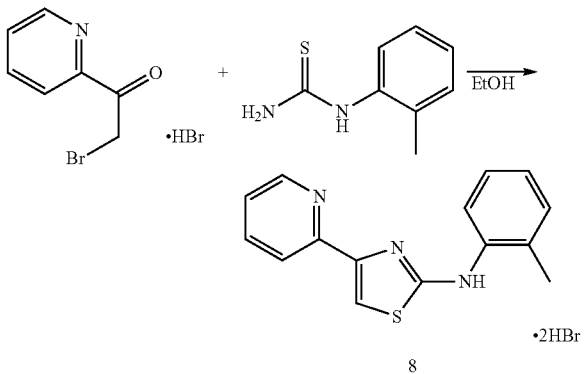

Specifically, a mixture of 2-(2-bromoacetyl)pyridine hydrobromide (56 mg. 10.20 mmol) and 1-(o-tolyl)thiourea (35 mg, 0.21 mmol) in ethanol (1 ml) was stirred at 70° C. for 6 h. After cooled to room temperature the mixture was evaporated and the residue was triturated with AcOEt. The solid was collected by filtration to give compound 8 (80 mg, 93% yield as dihydrobormide salt). $^1$H NMR (300 MHz. DMSO-d$_6$)δ 9.70(s. 1H), 8.73(d, J=5.7, 1H). 8.52 (t, J=7.7, 1H), 8.45 (d, J=7.8, 1H), 8.21-8.11 (m, 1H), 8.03-7.94 (m, 1H), 7.91-7.80 (m, 1H), 7.26 (t, J=6.8, 2H), 7.14-7.03 (m, 1H), 2.30 (s, 3H).

Synthesis of 5-chloro-N-(3-methylpyridin-2-yl)-4-(pyridin-2-yl)thiazol-2-amine (16). The compound was prepared according to the following scheme:

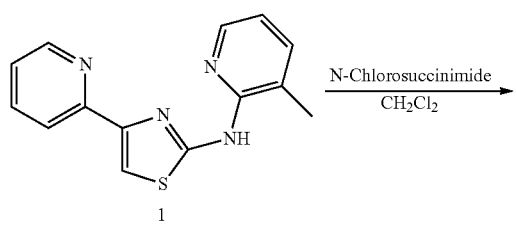

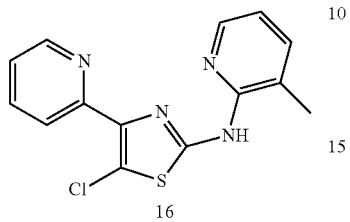

Specifically, a mixture of N-(3-methylpyridin-2-yl)-(pyridin-2-yl)thiazil-2-amine 1 (54 mg, 0.20 mmol) and N-chlorusuccinimide (32 mg, 0.24 mmol) in dichloromethane (2 ml) was stirred at room temperature for 64 h. After diluted with dichloromethane, the mixture was washed with saturated aqueous sodium bicarbonate and saturated aqueous sodium chloride, dried over anhydrous sodium sulfate and evaporated. The residue was chromatographed on a silica gel (ethyl acetate:chloroform=1:4–1:2) to give compound 16 (57 mg, 93% yield). $^1$H NMR (400 MHz, DMSO-d6)δ 10.86(s, 1H), 8.70-8.65 (m, 1H), 8.23-8.18 (m, 1H), 8.01 (d, J=7.6 Hz, 1H), 7.92 (t, J=7.5 Hz, 1H), 7.60 (d, J=6.7 Hz, 1H), 7.41-7.35 (m, 1H), 6.99-6.93 (m, 1H), 2.36 (s, 3H). Rt 1.34 min, MS +303.0/304.9.

Synthesis of 5-bromo-N-(3-methylpyridin-2-yl)-4-(pyridin-2-yl)thiazol-2-amine (17). The compound was prepared according to the following scheme:

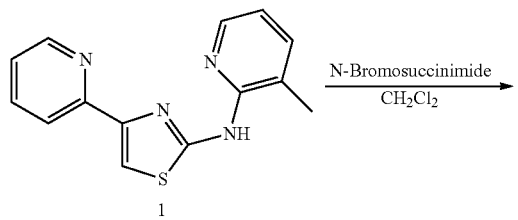

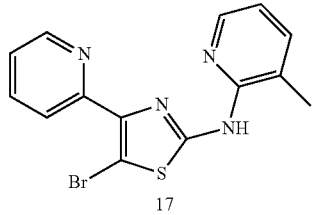

Specifically, a mixture of N-(3-methylpyridin-2-yl)-4-(pyridin-2-yl)thiazol-2-amine 1 (54 mg, 0.20 mmol) and N-bromosuccinimide (42 mg, 0.24 mmol) in dichloromethane (10 ml) was stirred at room temperature for 70 min. After diluted with dichloromethane, the mixture was washed with saturated aqueous sodium bicarbonate, dried over anhydrous sodium sulfate and evaporated. The residue was chromatographed on a silica gel (ethyl acetate:chloroform=1:4–1:2) to give compound 17 (60 mg, 86% yield). $^1$H NMR (400 MHz, DMSO-d$_6$)δ 10.89 (s, 1H), 8.67 (d, J=3.4Hz, 1H), 8.21 (d, J=3.8 Hz, 1H), 8.02 (d, J=7.6 Hz, 1H), 7.91 (t, J=7.5 Hz, 1H), 7.60(d, J=6.6 Hz, 1H), 7.42-7.35 (m, 1H), 6.99-6.93 (m, 1H), 2.36 (s, 3H). Rt 1.38 min, MS +346.9/348.8.

Synthesis of ethyl 2-((3-methylpyridin-2-yl)amino)-4-(pyridin-2-yl)thiazole-5-carboxylate (18). The compound was prepared according to the following scheme:

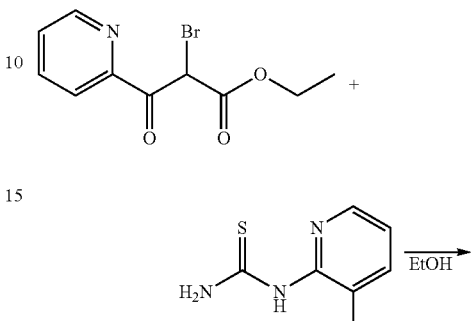

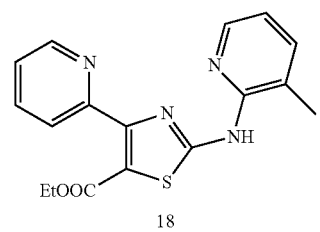

Specifically, a mixture of ethyl 2-bromo-3-oxo-3-(pyridio-2-yl)propanoate (142 mg, 0.52 mmol) and 1-(3-mecthylpyridin-2-yl)thiourea (88 mg, 0.53 mmol) in ethanol (5 ml) was stirred at 70° C. for 2 h. After cooled to room temperature, the reaction was quenched with saturated aqueous sodium bicarbonate (5 ml) and the mixture was evaporated to about a half of its volume. Water (5 ml) was added and the mixture was extracted with chloroform. Organic phase was washed with saturated aqueous sodium chloride, dried over anhydrous sodium sulfate and evaporated. The residue was crystallized from ethanol to give compound 18 (100 mg) and the mother liquor was chromatographed on a silica gel (ethyl acetate:hexanes=1:2–1:1) to give additional compound 18 (67 mg, total 167 mg, 94% yield). $^1$H NMR (300 MHz, DMSO-d$_6$)δ 11.18 (s, 1H), 8.62 (d, J=4.8 Hz, 1H), 8.30 (d, J=4.7 Hz, 1H), 7.87 (td, J=7.9, 1.6 Hz, 1H), 7.71-7.66 (m, 1H), 7.64 (d, J=7.4 Hz, 1H), 7.46-739 (m, 1H), 7.01 (dd, J=7.2, 5.1 Hz, 1H), 4.14 (q, J=7.0 Hz, 2H), 2.36(s, 3H), 1.14 (t, J=7.1 Hz, 3H). Rt 1.24 min, MS +341.0.

Synthesis of N-(3-methylpyridin-2-yl)-5-(morpholinomethyl)-4-(pyridin-2-yl)thiazol-2-amine (19). The compound was prepared according to the following scheme:

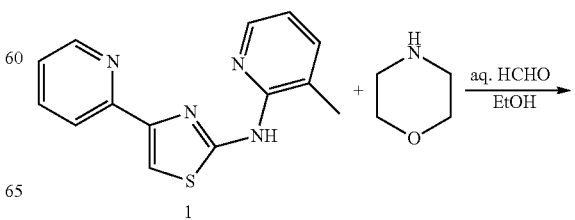

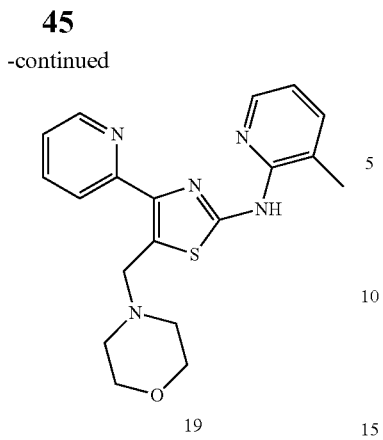

19

Specifically, a mixture of N-(3-methylpyridin-2-yl)-4-(pyridin-2-yl)thiazol-2-amine 1 (113 mg, 0.42 mmol), morpholine (367 μl, 4.21 mmol), aqueous formaldehyde solution (36.5%, 341 μl, 4.21 mmol) in ethanol (2 ml) was stirred at 80° C. for 2 h. After cooled to room temperature, the mixture was diluted with ethyl acetate and washed with saturated aqueous sodium chloride, dried over anhydrous sodium sulfate and evaporated. The residue was chromatographed on a silica gel (chloroform:methanol=39:1 with 0.1% aqueous ammonia) followed by chromatographed on a silica gel (ethyl acetate:chloroform=1:4–1:1 with 0.1% triethylamine) to give compound 19 (144 mg, 93% yield). $^1$H NMR (400 MHz, DMSO-$d_6$)δ 10.25 (s, 1H), 8.65-8.59 (m, 1H), 8.22-8.17 (m, 1H), 8.04 (d, J=7.7 Hz, 1H), 7.87 (t, J=7.0 Hz, 1H), 7.55 (d, J=6.6 Hz, 1H), 7.33-7.25 (m, 1H), 6.94-6.87 (m, 1H), 4.21 (s, 2H), 3.59 (s, 8H), 2.35 (s, 3H). Rt 1.00 min. MS +368.1.

Synthesis of tert-butyl 2-((2-((4-(pyridin-2-yl)thiazol-2-yl)amino)pyridin-3-yl)oxy)acetate (20). The compound was prepared according to the following scheme:

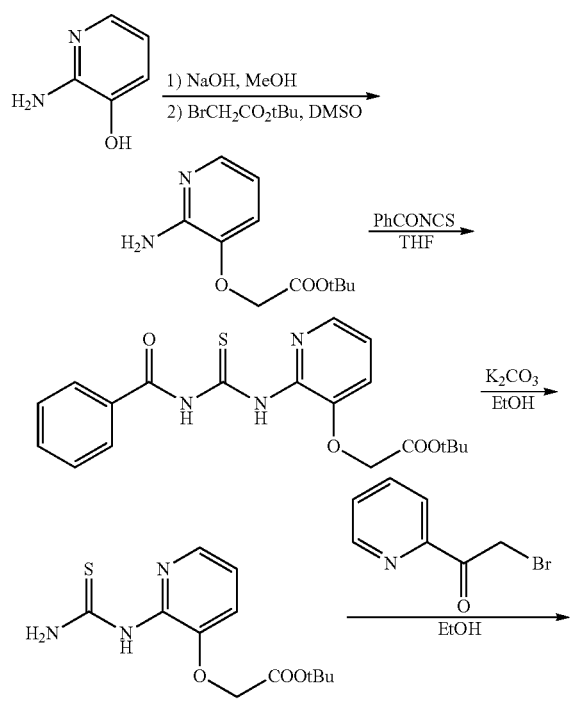

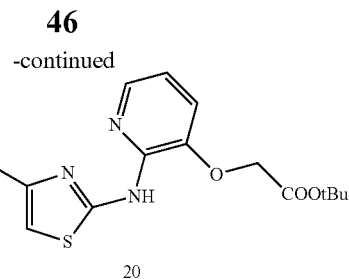

20

Specifically, a mixture of 2-aminopyridin-3-ol (551 mg, 5.00 mmol) and powdered sodium hydroxide (500 mg, 5.00 mg) in methanol (5 ml) was stirred at room temperature for 40 min. The mixture was evaporated to dryness. To the residue was added dimethyl sulfoxide (5 ml) and tert-butyl bromoacetate (807 μl, 5.50 mmol) and the mixture was stirred at room temperature for 20 h. The mixture was diluted with water and extracted with chloroform. Organic phase was washed with water and saturated aqueous sodium chloride, dried over anhydrous sodium sulfate and evaporated. The residue was chromatographed on a silica gel (ethyl acetate:hexanes=1:2–2:1) to give tert-butyl 2-((2-aminopyridin-3-yl)oxy)acetate (622 mg, 55% yield). $^1$H NMR (300 MHz, DMSO-$d_6$)δ 7.53 (d, J=5.0 Hz, 1H), 6.91 (d, J=7.8 Hz, 1H), 6.47 (dd, J=7.8, 5.0 Hz, 1H), 5.64 (s, 1H), 4.65 (s, 2H), 1.43 (s, 9H). Rt 0.69 min, MS +225.2.

To a solution of tert-butyl 2-((2-aminopyridin-3-yl)oxy) acotate (604 mg, 2.69 mmol) in tetrahydrofuran (5 ml) was added benzoyl isothiocyanate (410 μl, 3.01 mmol) and the mixture was stirred at 70° C. for 3.5 h. After cooled to room temperature, hexanes were added and the mixture was stirred at room temperature overnight. Resulting precipitates were collected by filtration, washed with a mixture of ethyl acetate and hexanes (1:5) and dried under vacuum to give tert-butyl 2-((2-(3-benzoylthioureido)pyridin-3-yl)oxy)acetate (902 mg, 86% yield). $^1$H NMR (300 MHz, DMSO-$d_6$)δ 8.09 (d, J=4.7 Hz, 1H), 8.00 (d, J=7.6 Hz, 2H), 7.69 (t, J=7.3 Hz, 1H), 7.61-7.50 (m, 3H), 7.33 (dd, J=8.2, 4.8 Hz, 1H), 4.85 (s, 2H), 1.41 (s, 9H). Rt 1.42 min. MS +388.2.

A mixture of (m-butyl 2-((2-(3-benzoylthioureido)pyridin-3-yl)oxy)acetate (895 mg, 2.31 mmol) and potassium carbonate (3.87 mg, 2.80 mmol) in ethanol (8 ml) was stirred at 70° C. for 9 h. After cooled to room temperature, water was added and the mixture was extracted with ethyl acetate. Combined extracts was washed with saturated aqueous sodium chloride, dried over anhydrous sodium sulfate and evaporated. The residue was chromatographed on a silica gel (ethyl acctate:chloroform=1:4–1:1) to give tert-butyl 2-((2-thioureidopyridin-3-yl)oxy)acetate (125 mg, 17% yield). $^1$H NMR (300 MHz, CDCl$_3$)δ 10.93 (s, 1H), 8.77 (s, 1H), 7.86-7.83 (m, 1H), 7.06-7.02 (m, 1H), 6.94 (dd, J=8.1, 5.0 Hz, 1H), 6.84 (s, 1H), 4.61 (s, 2H), 1.48 (s, 9H). Rt 1.24 min, MS +284.8.

A mixture of 2-(2-bromoacetyl)pyridine hydrobromide (126 mg, 0.45 mmol) and tert-butyl 2-((2-thioureidopyridin-3-yl)oxy)acetate 1-(3-methyl-2-pyridyl)thiourea (122 mg, 0.43 mmol) in ethanol (4 ml) was stirred at 70° C. for 3.5 h. After cooled to room temperature, the reaction was quenched with saturated aqueous sodium bicarbonate (7 ml) and the mixture was evaporated to about a half of its volume and extracted with ethyl acetate. Combined extracts was washed with water and saturated aqueous sodium chloride, dried over anhydrous sodium sulfate and evaporated. The residue was chromatographed on a silica gel (ethyl acetate: hexanes=1:2–1:0) to give compound 20 (146 mg, 88% yield). $^1$H NMR (300 MHz, DMSO d$_6$)δ 10.04 (s, 1H), 8.60

(d, J=4.7 Hz, 1H), 8.03 (d, J=7.9 Hz, 1H), 7.96 (d, J=5.0 Hz, 1H), 7.88 (td, J=7.7, 1.6 Hz, 1H), 7.70 (s, 1H), 7.39-7.28 (m, 2H), 6.96 (dd, J=7.9, 5.0 Hz, 1H), 4.85 (s, 2H), 1.43 (s, 9H). Rt 1.31, MS +385.9.

Synthesis of 2-((2-(((4-(pyridin-2-yl)thiazol-2-yl)amtno)pyridin-3-yl)oxy)acetic acid (21). The compound was prepared according to the following scheme:

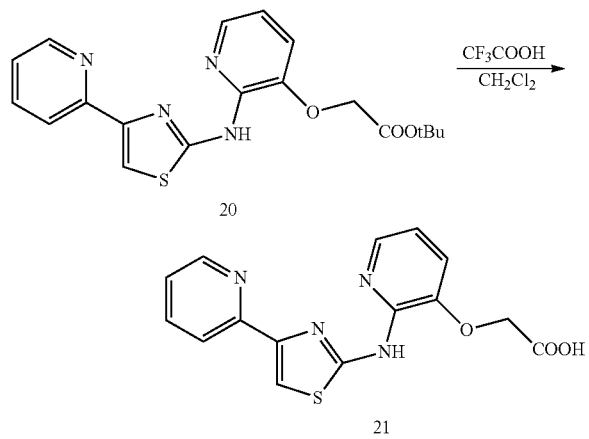

Specifically, a mixture of compound 20 (124 mg, 0.32 mmol), trifluroacetix acid (2 ml) and dichloromethane (3 ml) was stirred at room temperature for 2.5 h. The mixture was diluted with toluene and evaporated to dryness. The residue was triturated with ethyl acetate and the resulting precipitates were collected by filtration, washed with ethyl acetated and dried under vacuum to give compound 21 as mono trifluoroacetic acid salt (114 mg, 80% yield). $^1$H NMR (400 MHz, DMSO-$d_6$)δ 13.19 (s, 2H), 10.27 (s, 1H), 8.64 (d, J=3.7 Hz, 1H), 8.17 (d, J=7.7 Hz, 1H), 8.06 (t, J=7.0 Hz, 1H), 7.98 (d, J=4.6 Hz, 1H), 7.89 (s, 1H), 7.50-7.46 (m, 1H), 7.43 (d, J=7.8 Hz, 1H), 7.00 (dd, J=7.5, 5.0 Hz, 1H), 4.88 (s, 2H). Rt 0.84 min, MS +329.0.

Compounds 2-6 and 9-15 (see table below) disclosed herein could be made by similar methods, or by the schemes provided herein, or can be purchased commercially, for example, from Chembridge (San Diego, Calif.).

Example 3

The compounds were tested against replicating and non-replicating TB according to the assays described in Example 1. As can be seen some compounds can inhibit the growth of both replicating and non-replicating TB, whereas others are more selective or completely selective. The results are shown in the following table. Although Compound 16 has not yet been tested it is expected to have activity in the assays.

| Compound # | Structure | Replicating Mtb Log MIC IC90 (uM, GFP) | Non-replicating Mtb Carbon-starved MIC IC99 (uM, Luciferase) |
|---|---|---|---|
| 1 | 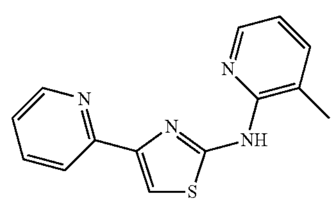 [SMILES: Cc1cccnc1Nc1nc(-c2ccccn2)cs1] | 0.5 | 1 |
| 2 | 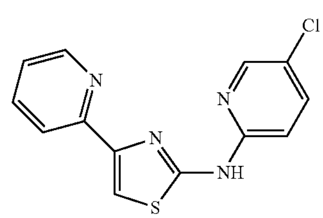 [SMILES: Clc1ccc(Nc2nc(-c3ccccn3)cs2)nc1] | 2 | 2 |
| 3 | 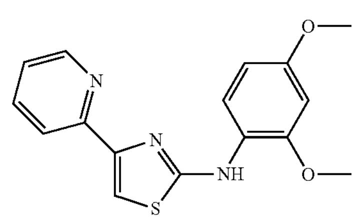 [SMILES: COc1ccc(Nc2nc(-c3ccccn3)cs2)c(OC)c1] | | 8 |

-continued
| Compound # | Structure | Replicating Mtb Log MIC IC90 (uM, GFP) | Non-replicating Mtb Carbon-starved MIC IC99 (uM, Luciferase) |
|---|---|---|---|
| 4 | 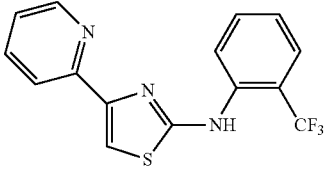 [SMILES: FC(F)(F)c1ccccc1Nc1nc(-c2ccccn2)cs1] | 62 | |
| 5 | 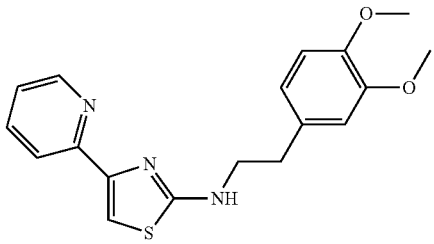 | 62 | 8 |
| 6 | 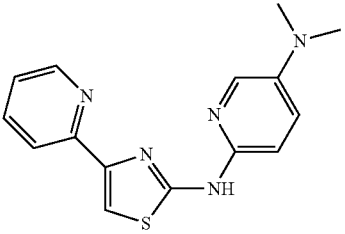 [SMILES: CN(C)c1ccc(Nc2nc(-c3ccccn3)cs2)nc1] | 125 | 8 |
| 7 | 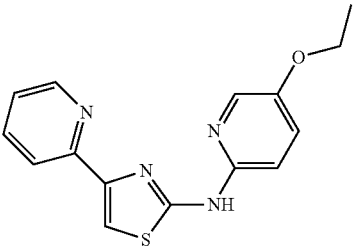 [SMILES: CCOc1ccc(Nc2nc(-c3ccccn3)cs2)nc1] | 62 | 16 |
| 8 | 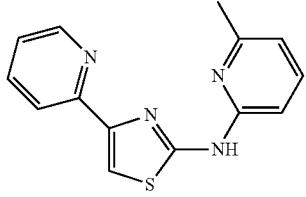 [SMILES: Cc1cccc(Nc2nc(-c3ccccn3)cs2)n1] | 31 | 2 |
| 9 | 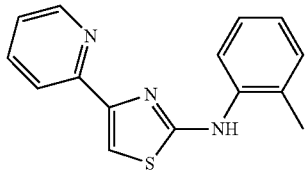 [SMILES: Cc1ccccc1Nc1nc(-c2ccccn2)cs1] | 62 | 8 |

-continued
| Compound # | Structure | Replicating Mtb Log MIC IC90 (uM, GFP) | Non-replicating Mtb Carbon-starved MIC IC99 (uM, Luciferase) |
|---|---|---|---|
| 10 | 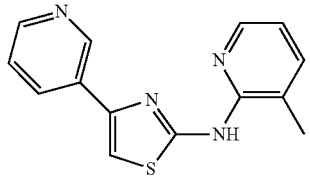 [SMILES: Cc1cccnc1Nc1nc(-c2cccnc2)cs1] | | 125 |
| 11 | 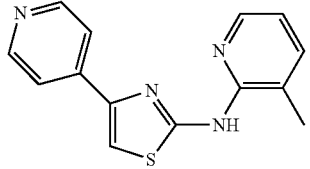 [SMILES: Cc1cccnc1Nc1nc(-c2ccncc2)cs1] | | None detected |
| 12 | 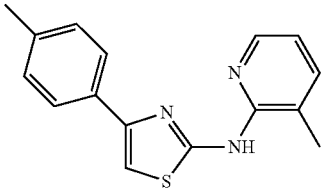 | | 125 |
| 13 | 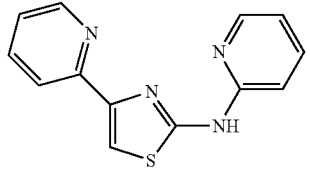 [SMILES: c1ccc(Nc2nc(-c3ccccn3)cs2)nc1] | | 8 |
| 14 | 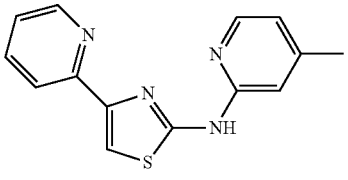 [SMILES: Cc1ccnc(Nc2nc(-c3ccccn3)cs2)c1] | | 16 |
| 15 | 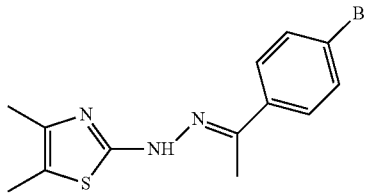 | 62 | 16 |
| 16 | 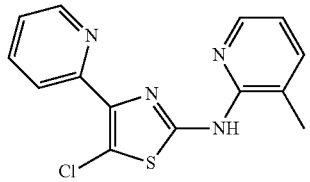 | | |

| Compound # | Structure | Replicating Mtb Log MIC IC90 (uM, GFP) | Non-replicating Mtb Carbon-starved MIC IC99 (uM, Luciferase) |
|---|---|---|---|
| 17 | 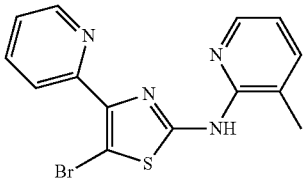 [SMILES: Cc1cccnc1Nc1nc(-c2ccccn2)c(Cl)s1] | <1 μM | <16 μM |
| 18 | 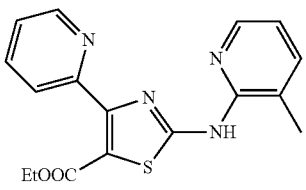 [SMILES: CCOC(=O)c1sc(Nc2ncccc2C)nc1-c1ccccn1] | 4 μM | 8 μM |
| 19 | 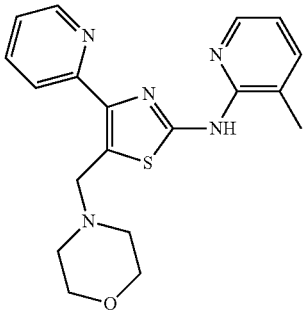 [SMILES: Cc1cccnc1Nc1nc(-c2ccccn2)c(CN2CCOCC2)s1] | 16 μM | 32 μM |
| 20 | 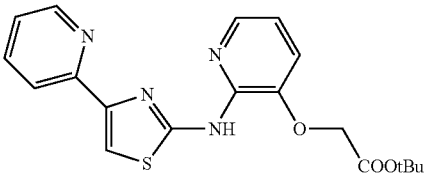 | N/A | 4 μM |
| 21 | 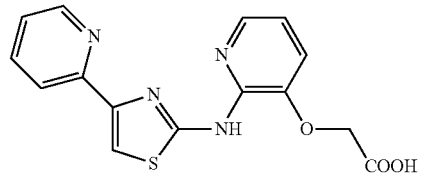 [SMILES: O=C(O)COc1cccnc1Nc1nc(-c2ccccn2)cs1] | 125 μM | >125 μM |

What is claimed is:

1. A method of treating non-replicating tuberculosis comprising administering to a subject a compound of Formula I, or a pharmaceutically acceptable salt or ester thereof:

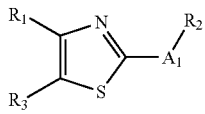

wherein:

$R_1$ is a substituted phenyl or a pyridyl;

$R_2$ is substituted phenyl or optionally substituted pyridyl; and $R_3$ is H, halo, or alkoxycarbonyl.

2. The method of claim 1, wherein the compound is selected from the group consisting of:

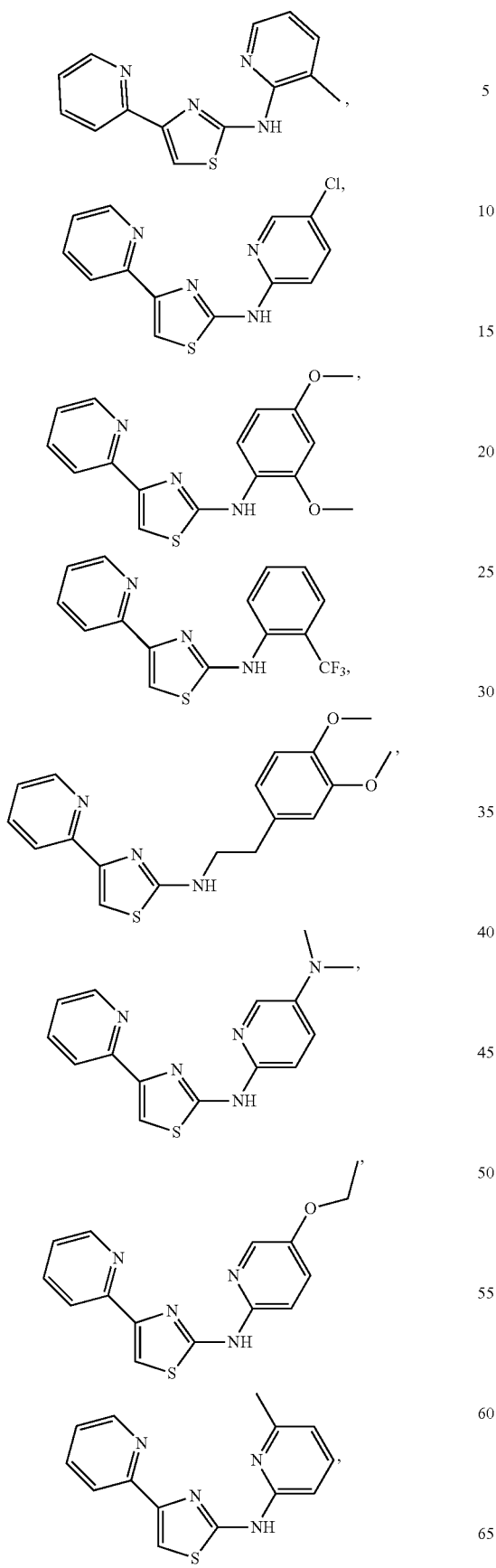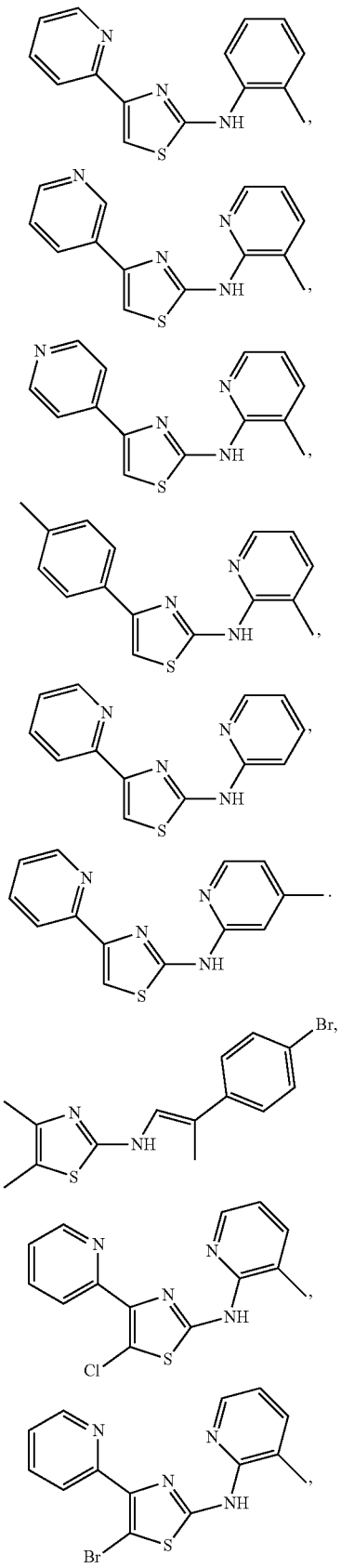

-continued

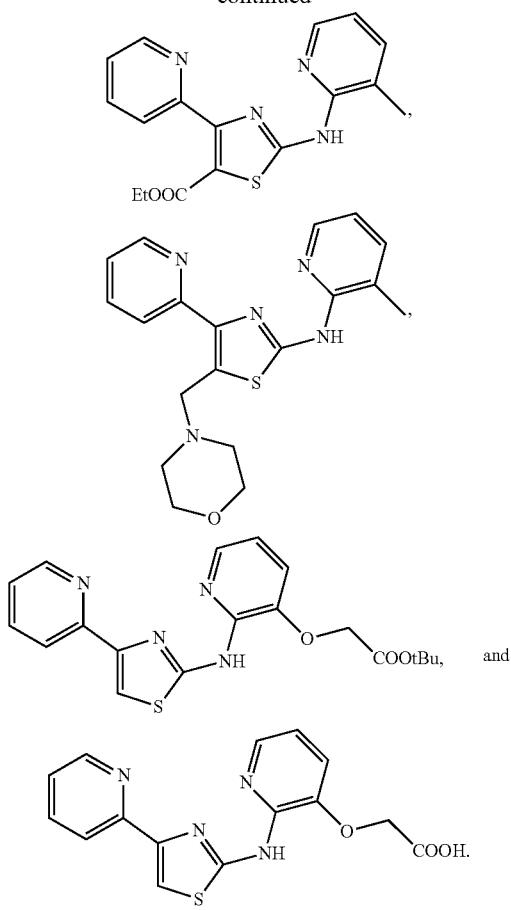

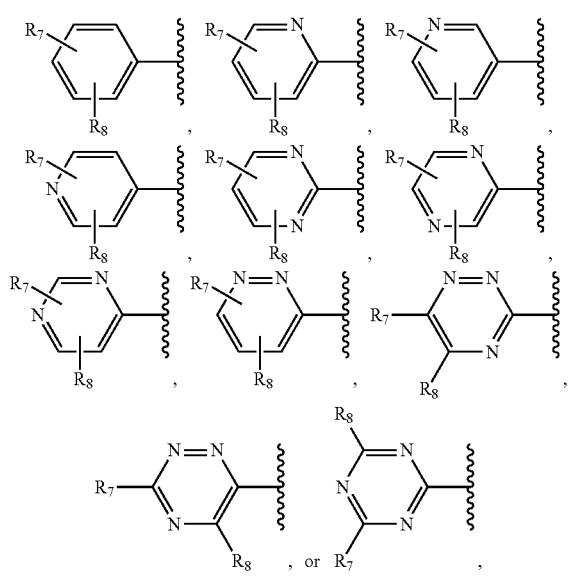

3. The method of claim 1, wherein in the compound Of Formula I, $R_3$ is H or halo.

4. The method of claim 1, wherein in the compound of Formula I, $R_1$ is:

wherein:
$R_7$ and $R_8$ are each independently H or alkyl.

5. The method of claim 1, wherein in the compound of Formula I, $R_1$ is

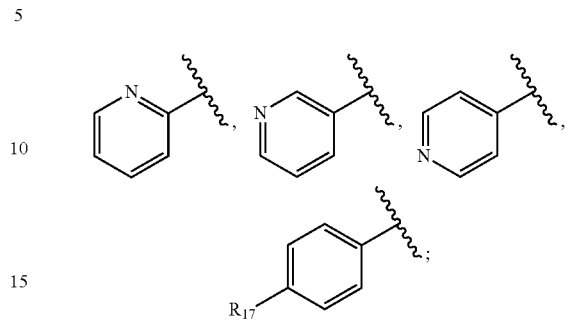

wherein $R_{17}$ is $C_1$-$C_6$ alkyl.

6. The method of claim 1, wherein in the compound of Formula I, $R_2$ is:

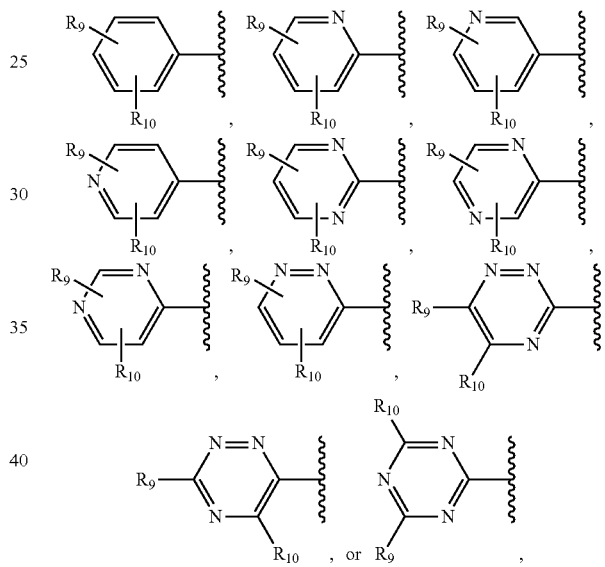

wherein:
$R_9$ and $R_{10}$ are each independently H, $OR_{14}$, $NR_{15}R_{16}$, halo, or optionally substituted alkyl; and
$R_{14}$, $R_{15}$, and $R_{16}$ are optionally substituted alkyl.

7. The method of claim 6, wherein in the compound of Formula I, $R_2$ is

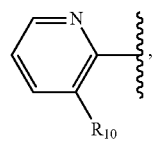

wherein:
$R_{10}$ is $C_1$-$C_6$ alkyl or —O—$R_{21}$—C(=O)$OR_{22}$;
$R_{21}$ is $C_1$-$C_6$ alkyl; and
$R_{22}$ is $C_1$-$C_6$ alkyl or H.

8. The method of claim 6, wherein in the compound of Formula I, $R_9$ and $R_{10}$ are independently H or $OR_{14}$.

9. The method of claim 6, wherein in the compound of Formula I, $R_9$ is H and $R_{10}$ is $C_1$-$C_6$ alkyl.

10. The method of claim 6, wherein in the compound of Formula I, $R_9$ and $R_{10}$ are independently H or halo.

11. The method of claim 6, wherein in the compound of Formula I, $R_2$ is

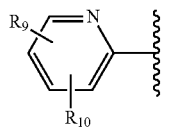

wherein $R_9$ and $R_{10}$ are independently H, halo, $OR_{14}$, $NR_{15}R_{16}$, or $C_1$-$C_6$ alkyl.

12. The method of claim 6, wherein in the compound of Formula I, $R_{15}$ and $R_{16}$ are $C_1$-$C_6$ alkyl.

13. The method of claim 1, wherein the compound of formula I is

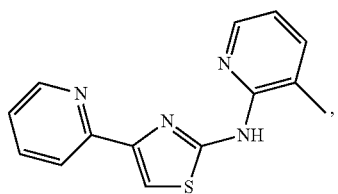 [SMILES: Cc1cccnc1Nc1nc(-c2ccccn2)cs1]

\* \* \* \* \*